(12) United States Patent
Aarabi

(10) Patent No.: US 9,687,155 B2
(45) Date of Patent: Jun. 27, 2017

(54) SYSTEM, METHOD AND APPLICATION FOR SKIN HEALTH VISUALIZATION AND QUANTIFICATION

(71) Applicant: Modiface Inc., Toronto (CA)

(72) Inventor: Parham Aarabi, Toronto (CA)

(73) Assignee: MODIFACE INC., Toronto (CA)

( * ) Notice: Subject to any disclaimer, the term of this patent is extended or adjusted under 35 U.S.C. 154(b) by 69 days.

(21) Appl. No.: 14/185,321

(22) Filed: Feb. 20, 2014

(65) Prior Publication Data

US 2015/0230712 A1     Aug. 20, 2015

(51) Int. Cl.
*A61B 5/00* (2006.01)

(52) U.S. Cl.
CPC ............ *A61B 5/0077* (2013.01); *A61B 5/444* (2013.01); *A61B 5/445* (2013.01); *A61B 5/6898* (2013.01); *A61B 5/725* (2013.01)

(58) Field of Classification Search
CPC ....... A61B 5/0077; A61B 5/444; A61B 5/445; A61B 5/725
See application file for complete search history.

(56) References Cited

U.S. PATENT DOCUMENTS

| | | | | |
|---|---|---|---|---|
| 2008/0194928 | A1* | 8/2008 | Bandic | A61B 5/411 600/306 |
| 2009/0245603 | A1* | 10/2009 | Koruga | A45D 44/00 382/128 |
| 2010/0185064 | A1* | 7/2010 | Bandic | A61B 5/0059 600/306 |
| 2010/0232773 | A1* | 9/2010 | DePaula | G03B 15/00 396/5 |
| 2011/0213253 | A1* | 9/2011 | Kruglick | A61B 5/444 600/477 |
| 2012/0008838 | A1* | 1/2012 | Guyon | G06F 19/345 382/128 |
| 2012/0078088 | A1* | 3/2012 | Whitestone | A61B 5/441 600/425 |
| 2015/0044098 | A1* | 2/2015 | Smart | A61B 5/0013 422/82.05 |
| 2015/0051921 | A1* | 2/2015 | Tran | G06F 19/322 705/3 |
| 2015/0065803 | A1* | 3/2015 | Douglas | A61B 1/00009 600/200 |
| 2015/0186518 | A1* | 7/2015 | Kusumoto | G06Q 30/0631 709/203 |

* cited by examiner

*Primary Examiner* — Baisakhi Roy
(74) *Attorney, Agent, or Firm* — Gowling WLG (Canada) LLP

(57) ABSTRACT

The present invention is a system, method and application for skin health visualization and quantification. The present invention is operable to process an image or video showing skin of a subject to determine characteristics of the skin through a quantitative measuring of parameters. The image or video is processed and analyzed a software application executed by a system incorporating a computer processor, data storage and display unit. A camera may further be integrated system. One or more filters applied to the image or video, to identify characteristics of the skin. A result of skin health results and overall skin health is generated. The image or video, skin health results and/or overall skin health may be displayed to a user. A visualization of amplifications or attenuations of skin health may further be displayed to a user. The invention may be wholly provided in a mobile device.

18 Claims, 16 Drawing Sheets

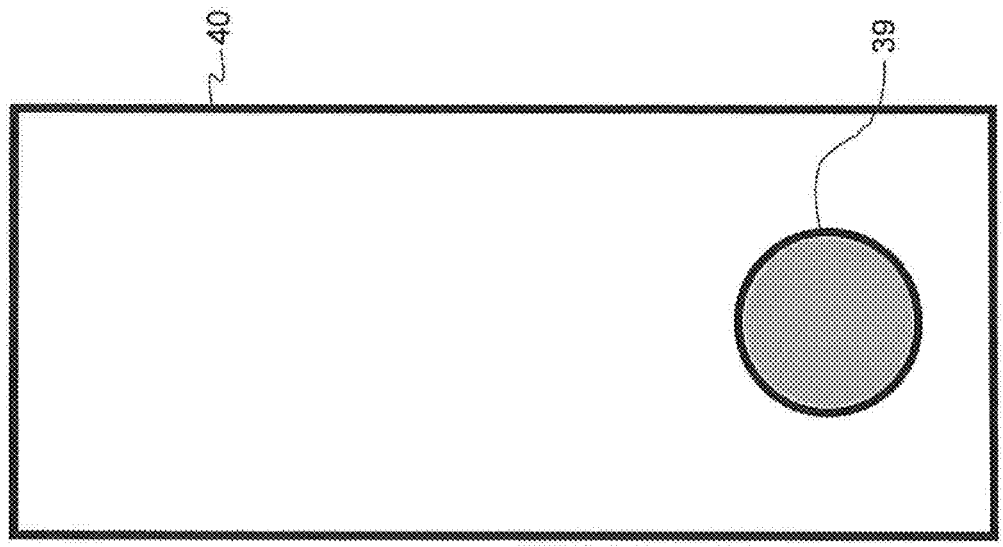
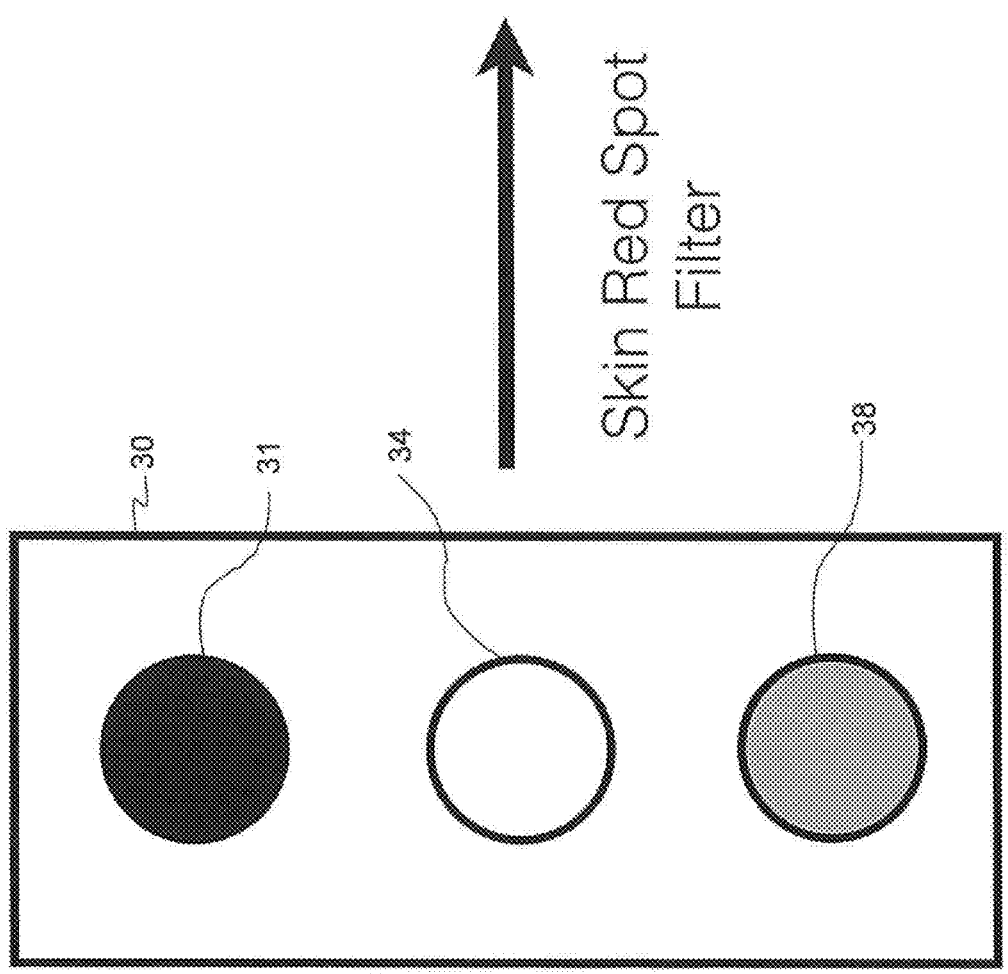
FIG. 5

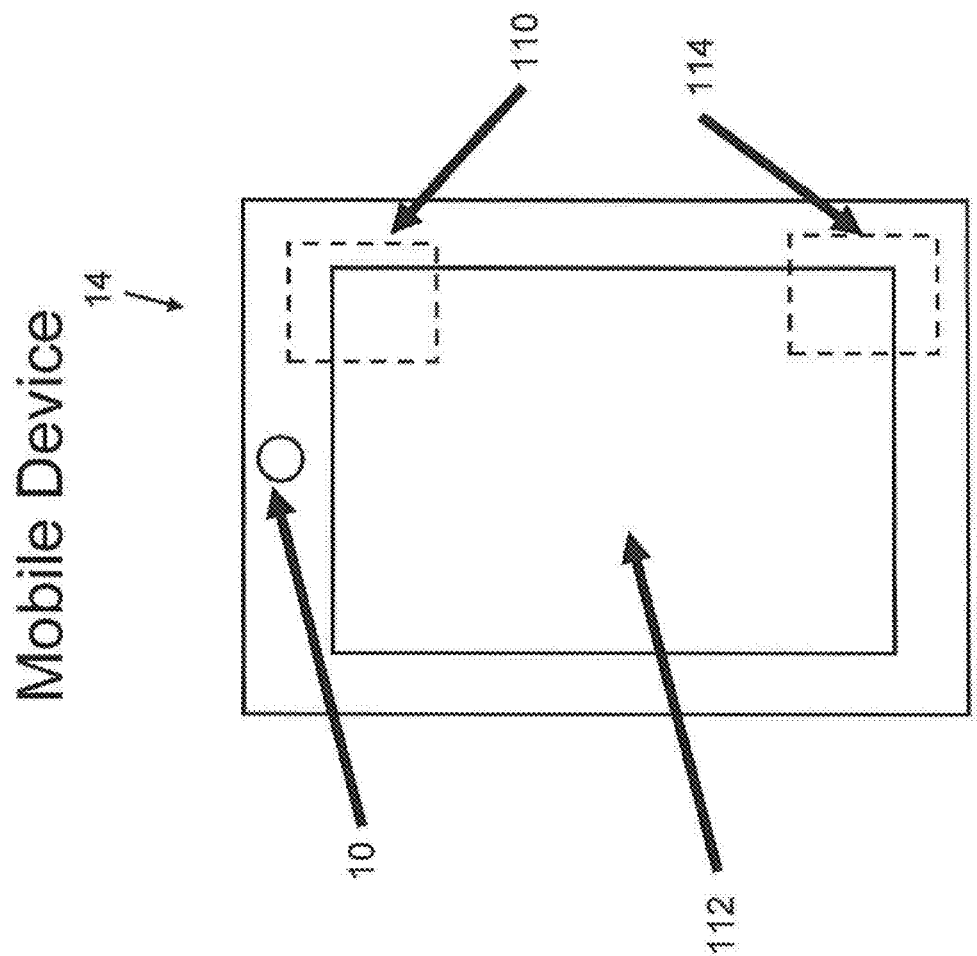

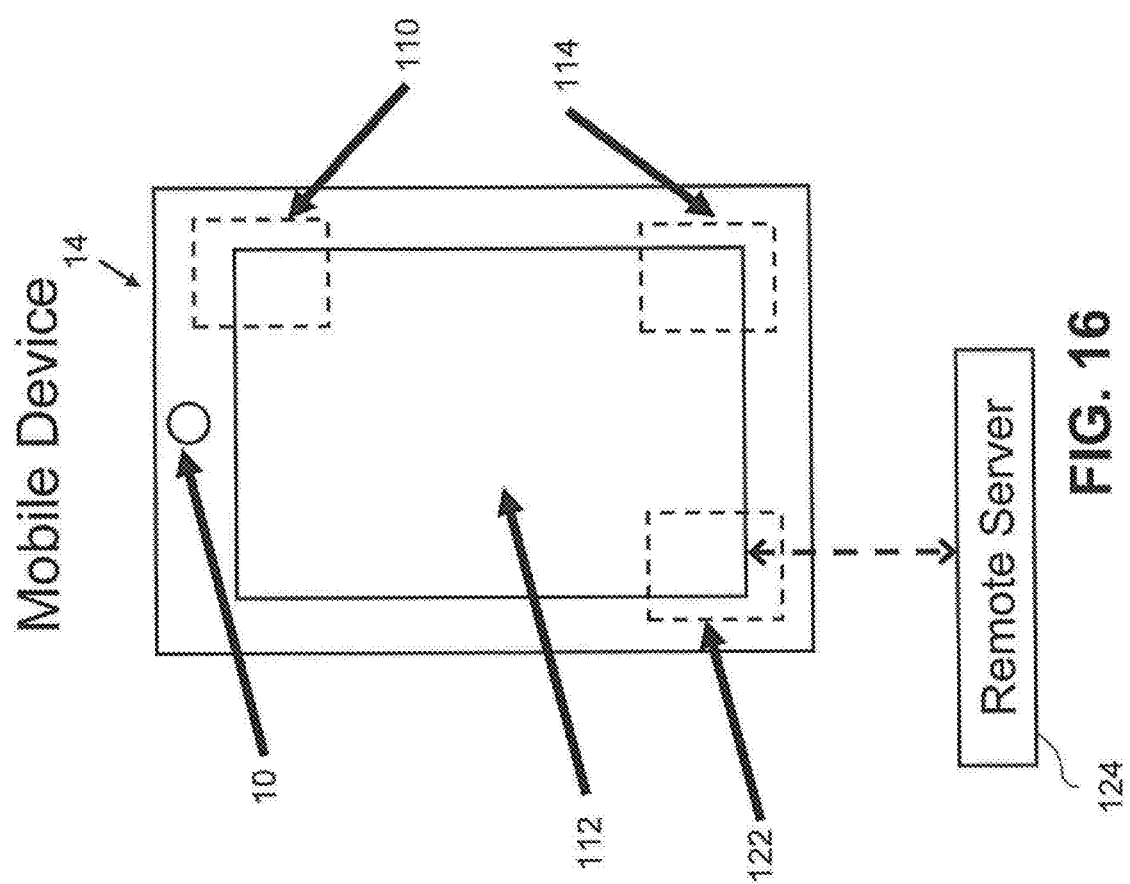

SYSTEM, METHOD AND APPLICATION FOR SKIN HEALTH VISUALIZATION AND QUANTIFICATION

FIELD OF INVENTION

This invention relates in general to the field of a system and method for analyzing the condition of skin and more specifically to utilize an image or video segment showing an area of skin for the purpose of the analysis and to produce representations of the skin in a more deteriorated or ameliorated state.

BACKGROUND OF THE INVENTION

Monitoring the health of skin is extremely important to a person or animal's overall health. Conditions such as Psoriasis, dryness, sun burn, moles, discoloration, flakes, redness, or other conditions affecting skin can trigger pain and discomfort. Skin conditions can also lead to or be an indicator for series health risks in some instances.

Utilizing digital and electronic means of capturing images or video segments showing areas of skin, and to undertake analysis or modelling of skin conditions can offer an efficient and effective tool in the monitoring skin health. The prior art includes some devices and methods directed to analysis of skin. Notably, these prior art examples are generally directed to a narrow analysis of a specific skin condition.

PCT Application No. PCT/IB2009/054811 (Publication No. WO 2010049907 A2), as filed on Oct. 20, 2009, discloses the invention "A portable skin diagnosis device". The invention is a portable skin diagnosis device that incorporates elements to collect an optical measurement and a non-optical measurement. The optical and non-optical measurements are combined to establish a diagnosis. The optical measurement in particular is directed to skin pigmentation and aging. Characteristics of the skin may be identified through use of one or more conversion matrices to determine such characteristics from the measurements. In particular, the device is to be used for a diagnosis about the pigmentary status of the skin focusing on the colour and behaviour of the skin with regard to the sun and its chromophores. Notably, this prior art does not disclose any combination of images, the application of filters to product new images, or the amplification or attenuation of different skin filters for visualizing specific effects on the skin. In order to function as disclosed, the invention requires that a skin sample be positioned in proximity to the device. Thus, the disclosure is narrowly focused upon the elements that make up the device, being elements for the purpose of identifying skin pigmentation and aging in a skin sample proximate to the device.

PCT Application No. PCT/US2006/048237 (Publication No. WO 2007075565 A2), as filed on Dec. 18, 2006, (corresponding to U.S. Patent Application Publication No. 2009/0220415 published on Sep. 3, 2009) discloses the invention "Diagnostic system for the detection and diagnosis of skin cancer". This prior art discloses methods and compositions for analysis of skin surfaces to specifically determine the presence of neoplastic tissue. To utilize this invention a composition that is a florescent probe that binds to a specific neoplasia associated marker is applied topically to an area of interest on a subject's skin. The binding is detected by a compact illumination that provides illumination at a wavelength appropriate for image acquisition. An image is captured of the area of investigation so illuminated. The image is analyzed to identify, characterize and distinguish non-malignant and malignant skin lesions. Thus, the disclosure requires that the skin sample be treated with the composition in order for the invention to be able to achieve its purpose of detecting neoplasia associated proteins. Thus, the disclosure is focused on a process that requires particular steps to occur for the invention to function, including administration of a composition to an area of skin, specific illumination of the area, and capture of an image of the illuminated area. The image is then analyzed to identify skin cancer in the skin in the image.

PCT Application No. PCT/US2013/034410 (Publication No. WO 2013149038 A1), as filed on Mar. 28, 2013, discloses the invention "Methods and software for screening and diagnosing skin lesions and plant diseases". The invention is a system for the identification and/or classification of an object of interest on a body. An imaging device is utilized to produce an image and a library of algorithms or modules are implemented to process the image and classify objects of interest on the skin based on representative features. Thus, the disclosure is directed solely to identifying and classifying objects on a body.

PCT Application No. PCT/IB2012/057558 (Publication No. WO 2013093851 A1), as filed on Dec. 20, 2012, discloses the invention "Method for delivering cosmetic advice". This invention is a cosmetic method to identify indications relating to the skin of a region, or a body, of an individual for the purpose of providing cosmetic advice relating to skin colour. The invention requires that a colour image be captured from a region, or a body, of an individual and that the image also has a colour reference chart in the field of the image. The colour in the image is utilized to determine an indication, such as skin type, skin colour relating to a pigmentation or a depigmentation process, appropriate photo-protection, or a product that may be applied or administered to temporarily modify the colour of the individual's skin in the body region in the image. Thus, the disclosure is narrowly directed to a determination of skin colour and possible pigmentation or depigmentation, and products related thereto.

PCT Application No. PCT/US2010021529 (Publication No. WO 2010093503 A2), as filed on Jan. 20, 2010, discloses the invention "Skin analysis methods". The invention is a device for performing an analysis of digitally captured skin characteristics for the purpose of producing a skin condition assessment, skin regimen recommendation, and skin regimen effectiveness tracking. The device is operable to direct incident electromagnetic radiation to a location on the skin of a user. The device further incorporates a radiation detector operable to measure various parameters of radiation re-emitted from the location. A skin condition analysis module coupled to the detector operates to generate a skin condition assessment, based partly on at least one of RGB analysis and diffused reflectance analysis of the radiation parameters.

SUMMARY OF THE INVENTION

In one aspect, the present disclosure relates to a skin health system operable to process and analyze one or more images or video showing a subject's skin in accordance with a software application, said skin health system comprising: a computer processor operable to receive the one or more images or video and to process and analyze the one more images or video in accordance with commands of the software application to determine skin health results and overall skin health of the subject's skin shown in the one or more images or video; a data storage to store the one or more images or video and processing and analysis output of the computer processor including the skin health results and overall skin health; and a display operable to display any of the one or more images or video to a user, and to further display the processing and analysis output of the computer processor to the user, including the skin health results and overall skin health of the subject's skin shown in the one or more images or videos.

Said aspect of the present disclosure further relating to a camera being integrated in the skin health system, said camera being operable to capture the one or more images or video.

Said aspect of the present disclosure further relating to incorporating the skin health system in a mobile device.

Said aspect of the present disclosure further relating to the mobile device being a smartphone, tablet, or laptop computer.

Said aspect of the present disclosure further relating to the mobile device incorporating a transmission means operable to transmit data from and to the skin health system and a remote server.

Said aspect of the present disclosure further relating to the mobile device being connected to one or more of the following: a remote processor; a remote data storage; and an external display.

Said aspect of the present disclosure further relating to the camera being integrated in a rotational apparatus operable to rotate the camera around a subject so the camera can capture the one or more images or video while rotating around the subject.

In another aspect, the present disclosure relates to a skin health analysis method operable to determine overall skin health of skin of a subject shown in one or more images or video, comprising the steps of: a computer processor receiving the one or more images or video and said computer processor performing the following steps for each of the one more images or video frames of the video to determine skin health results for each of the one or more images or video frames of the video; blurring the image or video frame to produce a blurred image or video frame and utilizing said lured image or video frame to determine an average skin colour or average skin patch; determining the depth or texture results of the image or video frame through an analysis of colour channels in the image or video frame; determining the peel and flake results of the image or video frame; and determining redness results of the image or video frame; and the computer processor utilizing the skin health results to determine the overall skin health of the skin shown in the one or more images or video; displaying the overall skin health and one or more skin health results to a user, and storing one or more of the following in a data storage as previous skin health analysis information: at least one of the one or more images or video; the overall skin health; and at least one of the skin health results.

Said aspect of the present disclosure further comprising the step of generating one or more visualizations depicting amplification or attenuation of any of the skin health results.

Said aspect of the present disclosure further comprising the step of applying one or more filters to each of the one or more images or video frames of the video to produce filtered images that highlight and identify specific characteristics of each of the one or more images or video frames.

Said aspect of the present disclosure further comprising the step of applying one or more of the following filters to each of the one or more images or video frames of the video: a dark spot filter to identify dark spots; a white spot filter to identify white spots; and a red spot filter to identify red spots.

Said aspect of the present disclosure further comprising the step of utilizing the filtered images to determine skin conditions or skin issues relating to the skin shown in each of the one or more images or video frames, including peeling skin, flaky skin, dry skin, red skin, shadowed skin, or darkened skin.

Said aspect of the present disclosure further comprising the further steps of utilizing the components of a mobile device to facilitate the steps of the method; and utilizing the camera of the mobile device to capture the one or more images or video.

Said aspect of the present disclosure further comprising the steps of: applying weighted averages to each of the skin health results to produce weighted average results; and utilizing the weighted average results to determine the overall skin health.

Said aspect of the present disclosure further comprising the steps of: generating skin health scores based on the skin health results and the overall skin health; and reporting the skin health scores to the user by displaying the skin health scores to the user on the display unit.

Said aspect of the present disclosure further comprising the step of generating one or more screens incorporating skin heath results and overall skin health, said screens being operable for the user to navigate through the one or more screens to access skin health results and overall skin health when said one or more screens are displayed to the user.

Said aspect of the present disclosure further comprising the steps of: generating skin health questions and displaying said skin health questions to a user; receiving a response to each of the skin health questions provided by the user; utilizing each response in combination with the skin health results to determine the overall skin health.

Said aspect of the present disclosure further comprising the steps of: accessing the previous skin health analysis information relating to the subject from the data storage; displaying the previous skin health analysis information to a user on the display unit with any of the skin health results and the overall skin health; and analyzing the previous skin health analysis information and the skin health results and overall skin health to determine any improvement or deterioration of any skin condition or skin issue of the subject.

Said aspect of the present disclosure further comprising the steps of: displaying the one or more images or video and the skin health results and overall skin health to a user, said user being a skin health professional; and the skin health professional utilizing the one or more images or video, the skin health results and overall skin health to diagnose one or more skin conditions of the subject.

In another aspect, the present disclosure relates to a computer program product comprising a non-transitory computer readable medium bearing software instructions, said software instructions being operable to enable a computer processor to perform predetermined operations, said computer processor being linked to a data storage, said computer program product comprising: a processing and analysis module operable to process and analyze one or more images or video transmitted to the computer processor to determine overall skin health of the skin shown in the one or more images or video; a display module operable to produce a display any of the one or more images or video to a user via a display unit, and to further produce a display of information relating to the overall skin health of the skin shown in the one or more images or video and related information to a user via a display unit; and a data storage module operable to prepare data to be transmitted from the computer processor for storage in the data storage.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The invention will be better understood and objects of the invention will become apparent when consideration is given to the following detailed description thereof. Such description makes reference to the annexed drawings wherein:

FIG. 5 shows a skin filter operable to detect red spots on skin, in accordance with an embodiment of the present invention.

FIG. 15 shows a mobile device of an embodiment of the present invention.

FIG. 16 shows a mobile device connected to a remote server, in accordance with an embodiment of the present invention.

Figure 1:
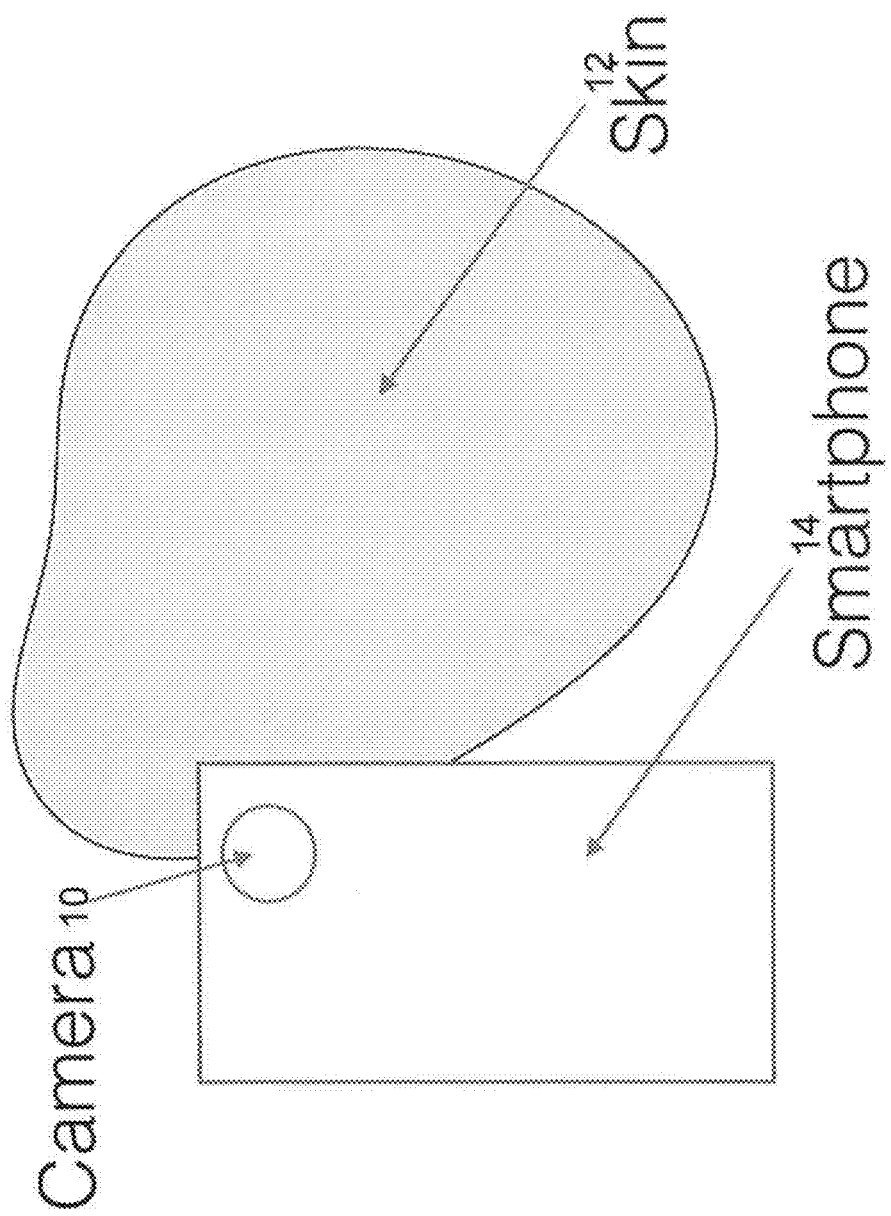
FIG. 1 shows the positioning of a device incorporating a camera in relation to skin, said camera being operable to capture an image or video of said skin, in accordance with an embodiment of the present invention.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

The present invention is a system, method and application for skin health visualization and quantification. The present invention is operable to process an image or video showing skin of a person or animal (i.e., a subject) to determine characteristics of the skin. The image or video may be captured by a camera, such as a camera available on a smart phone, or any other device capable of capturing an image or a video. The image or video is processed by an application that may be stored in the device, or otherwise accessed by the device. The characteristics of the skin are identified through a quantitative measuring of parameters achieved by the application. This may involve the utilization of one or more filters applied to the image or video, each filter being utilized to identify one or more characteristics of the skin and to determine or estimate parameter measures relating to such characteristics. The parameter measures may be utilized to generate skin health results and/or overall skin health relating to the skin in the image or video. The skin health results and/or overall skin health may be displayed to a user.

The skin health results and overall skin health may be provided in the form of scores. Both scores and results can be generated by the preset invention relating to skin health (i.e., as generated from individual images or video frames), as well as overall skin health. Herein references to scores should be read to indicate both results and scores for a particular measure of skin health or overall skin health also generated by the present invention.

A visualization module may further be incorporated in the present invention whereby a visualization of estimations of what the skin shown in the image or video would look like if the skin health improves or deteriorates in relation to a particular skin condition is shown to the user.

References to "an image" captured by the camera in the present invention should be understood by the reader to include plural "images" captured by a camera of skin of the same subject. The present invention may analyze any of the following; an image, multiple images or video that is captured by the camera or otherwise provided to the invention. However, for ease of reference, in this document generally reference is made to "an image" should be read to include a singular image or multiple images, and a reference to "video" should be read to include multiple video frames. Multiple images showing the skin of the same subject may be read to be a set of images.

Additionally, reference to the "capture of an image or video" may also relate to a scan that produces an image or video relating to the scan of an area of a subject's skin.

Generally the method of the present invention includes several steps to analyze the condition of skin shown in an image or video. The method may be performed by a set of modules, including a processing and analysis module, a display module and a data storage module.

A video or image is captured showing an area of skin, such as a patch of skin, through the use of a camera. The camera may be a camera incorporated in a device, such as a smartphone. The video or image is in a digital format. The video or image is analyzed by the system of the present invention, and in particular by the processing and analysis module of the present invention. The analysis involves the generation of a quantitative measure of one or more parameters relating to the skin shown in the video or image, for example, such as the level of flakiness, dryness, shadows, and/or redness of the skin. The analysis can also produce estimated quantitative measurements relating to the skin when the image or video lacks information required to generate a more certain quantitative measurement of one or more parameters relating to the skin.

Based on the parameter measurements, or estimated parameter measurements, certain skin health results relating to each parameter may be determined and provided to a user as information or a score. Furthermore, the skin health results relating to parameters may be processed and combined to determine overall skin health information that can be reported to the user. In embodiments of the present invention, the overall skin health can include the determination of information relating to skin health and/or scores relating to overall skin health. Any of the information or scores relating to overall skin health may be provided to a user.

In some embodiments of the present invention user responses to queries provided to the user relating to skin health may also be utilized to determine skin health information relating to specific skin conditions, and the user responses may further be utilized to generate skin health results and an overall skin health determination.

The overall health score provides a measurement of the overall level of health of skin shown in the image or video. A visualization estimation may also be generated so that a display is provided to the user indicating what the skin shown in the image or video would look like if the skin health either improves or deteriorates from that shown in the image or video. The visualization may be provided to be manipulated by the user to show varying levels of attenuation and amplification of skin health parameters of the subject's skin.

A user may view any report or other displayed information via a display unit or any type of device, including a smartphone or any other device capable of displaying information to a user. Displayed information may be generated and provided to the user by a display module of the present invention. In one embodiment of the present invention, if the image or video was captured through a camera incorporated in a smartphone, the same smartphone may be utilized by the user to view a display of a report, scores, results, or other information generated by the present invention. In some embodiments of the present invention, the whole of the system may be incorporated in a smart phone.

The system of the present invention may be configured in a variety of ways. Generally, the system incorporates the following elements: a computer processor comprising hardware operable to store a software application and to operate the software application and execute commands of the software application, and operable to receive an image or video; a display unit connected by way of a wireless or wired connection to the computer device whereby the user can view output generated by the software application; and a data storage means whereby the image or video and any skin health results, scores, overall skin health or other data received or generated by the system and method may be stored.

The system may further incorporate a camera operable to capture a digital image or video. The camera may be connected to the computer processor. An image or video transmission component may also be included that is operable to transmit the image or video captured by the camera from the camera. The transmission component may be integrated in the camera.

The camera is operable to capture an image or video showing skin. The image or video is transmitted by the transmission component to the computer device whereby it is accessible to the software application.

Upon receipt of the image or video the software application will process the image or video, and the processing will include an analysis of the image or video to generate the parameter measurements, or estimated parameter measurements, as skin health results, as discussed herein. The parameter measurements or estimated parameter measurements are utilized by the software application to generate overall skin health results, scores and/or other information, that is reported to the user by way of the display unit. The software application may further generate a visualization estimation that is displayed to the user by way of the display unit.

The configuration of the system of the present invention may be as separate elements that are located either remotely or closely in relation to one or more of the other elements of the system. The connections between elements of the invention may be wired or wireless.

In one embodiment of the present invention, the elements may be configured in a single mobile device, such as a smartphone that incorporates a computer device, display and camera, or any other individual device. The software application in such an embodiment of the present invention may be a mobile application. The mobile device may be configured to have connect-ability, through a wired or wireless connection, to a server that stores the software application of the present invention. The software application may be transmitted from the server, directly or via a connection means, such as an intranet, the Internet, or any other connection means, to the mobile device. The software application may be stored upon the computer device and/or other hardware components of the mobile device, or that are connected thereto, in a temporary or long-term manner. Alternatively, the mobile device may receive the software application and operate the software application without storing said software application.

The system of the present invention provides an executable software application to generate skin health analysis information, such as skin health results and overall skin health information.

In one embodiment, the invention is useful with software applications which provide application programming interfaces (APIs) such as transaction servers or messaging applications for distributed platforms providing connectivity (e.g., TCP/IP connectivity). The software application executes a set of instructions whereby a camera may be operated to capture an image or video, the image or video may be blurred, the original image or video may be subtracted from the blurred version of the image or video, and parameters may be identified and extracted from the result of the subtraction. The parameters may include redness, darkness, whiteness, or any other parameters that may be identified by the operation of the software application.

In some embodiments of the present invention, the parameters may consist of masks for multiple skin conditions or issues, for example, such as redness, darkness, and whiteness. The masks may be amplified or attenuated in the original image or video. The version of the image or video that is modified by the amplification or attenuation may be captured and stored as a new amplified or attenuated image or video. The amplified or attenuated image or video may be displayed to the user as a visualization of improvements or deteriorations of skin conditions in relation to the subject's present skin health. The amplification or attenuation of an image or video in accordance with creating a visualization of skin health improvement or deterioration is included as executable instructions in the software application.

The parameters may be processed and combined to generate a combined overall parameter that indicates aspects of the health of the skin shown in the image or video. The processing and combination of the parameters to produce the combined overall parameter may involve weighted averaging of each parameter. Weights will be applied to each parameter to represent the relative importance of each parameter. The weighted averaging may be applied to calculate an average from a single image or a video frame of the video. If there are additional images or video frames, the overall health skin score can be generated by a selected statistical combination of the skin health scores for each image or video frame. The statistical combination may involve either averaging a subset of the image or video frame parameters or determining the median of a subset of the parameters for the image or video frame.

Should there only be a single image for processing, then the overall skin health will be determined based upon the weighted averaging of the parameters for that single image, however, in the instance that a video with multiple video frames, or multiple images, are provided for processing, then the overall skin health will be determined based upon the weighted averaging involving all of the multiple video frames or multiple images, in accordance with the method described herein.

Embodiments of the present invention may further incorporate questions being posed to a user via the display unit of the system and a response means whereby the user provides one or more responses, and such response means is operable so that responses provided by the user via the response means are translatable and interpretable by the computer processor. For example, the response means (or communication means) may be a keyboard (e.g., touch screen keyboard, or other form of keyboard), a touch screen (capability of the display unit) whereby touching particular buttons or areas of the display unit may indicate specific responses, or any other means whereby a user can provide responses or instructions to the system of the present invention.

The questions posed to the user may include queries relevant to skin health, for example, such as the following: "Does your skin feel dry?", "Does your skin feel rough?", "Does your skin feel scaly?", "Is you skin unusually red?", or any other questions relevant to skin health. In an embodiment of the present invention that incorporates user responses, responses to such questions provided by the user via the response means may be combined with the parameters. The combination may be utilized to generate overall skin health. A weighted averaging of each parameter, as well as each user response to the questions posed, may be utilized, so that the parameters and user responses are processed and combined to determine the overall skin health. Alternatively any other statistical combination of the parameters and user responses may be utilized.

If a single image is utilized then the overall skin health will be determined based on the results from the processing of the single image. If multiple images or multiple video frames are processed, then a combination of these processed images and video frames may occur to generate the overall skin health. This will involve the weighted averaging or another statistical combination method being applied to the results from each of the images or video frames. The statistical combination may involve a statistical score addition or subtraction based on the user responses and either a subset of the image or video frame results, or taking the median of a subset of the image or frame results. Such an embodiment of the present invention provides output to a user based on both visual data (from the image or video) as well as a question-based skin health analysis.

Embodiments of the present invention, can include a system operable to utilize the software application that is configured in a variety of ways, such as any of the following: (i) all incorporated in a single mobile computing device, for example, such as a smartphone, tablet, or other mobile device; (ii) that includes a mobile computing device and an external server and the mobile device is operable to transmit information to, and receive information from, the server; or (iii) two or more elements of the system may be remotely located from each other and connected wirelessly or by a wired connection, so that information can be transmitted between elements so that each element can receive information from and transmit information to other elements as required for the function of the system as described herein. Any of these embodiments of the present invention may be operable to receive a software application to the computing device element of the system, and the computing device may be operable to execute instructions of the software application, and such instructions may involve functions of other elements.

The software application may be transmitted to the computing device that may be a laptop, tablet, desktop computer, mobile device, or any other computing device, or may be a computer processor or data storage of any type of device. Reference to the computing device herein should be understood to reference a "computer processor" or any other type of computing device operable to execute instructions of the software application of the present invention. Transmission of said software application may be achieved by a variety of means, for example, such as: directly from a transmitting server where the application is stored; via an Internet or intranet connection of the computing device so that the software application is downloaded via said connection to the computing device; or through a storage device, such as a hardware storage device, for example, such as a CD, DVD, hard disk, or other hardware storage device being connected to the computing device whereby the software application is either transmittable to the computing device, or accessible by the computing device. Updates, amendments or other modifications to the software application may also be transmitted to the computing device via any of the described means.

The software application may execute instructions to cause an image or video to be captured by a camera in some embodiments of the present invention, whereas in other embodiments of the present invention images or video may be transmitted to the software application and a camera will not be an element of the system of the present invention.

Any results relating to parameters, skin health results, overall skin health, scores relating to any of the foregoing, or any images or video, may be stored in a storage means.

A data storage module may facilitate such storage as well as accessing any stored data from any data storage means.

A skilled reader will recognize that the present invention offers several benefits and advantages over the prior art. For example, the prior art inventions do not provide a method for combining frames of a video or multiple images in the analysis of skin, whereas in the present invention frames of a video or multiple images may be combined to augment the accuracy and effectiveness of the analysis, as described herein.

As another example, the prior art does not incorporate the capture of skin health scores or results for individual frames of a video, or for applying skin filters to each frame to obtain new images and/or videos, as the present invention achieves. These aspects of the present invention are described herein.

As still another example, the prior art is not configured so as to allow a diagnosis of multiple skin conditions to be possibly made, as is possible based on the skin health results, overall skin health and visualizations of the present invention. Furthermore, the present invention allows for such diagnoses to be performed by a skin health professional located remotely from the user or the subject.

As yet another example, the prior art does not incorporate the amplification or attenuation of different skin conditions for visualizing specific effects on the skin, as is incorporated in the present invention. This aspect of the present invention is described here. In some embodiments of the present invention, filters may be applied to determine skin conditions. In some embodiments of the present invention, a user may be provided with an indicator (relating to a level) positioned along a scale whereby the user may move the indicator along the scale to alter a visualization of a subject's skin shown in an image so that improvements or deteriorations of certain skin conditions are shown in relation to such skin. The amplification or attenuation of skin conditions and the means of visualizing these provided by the present invention are particularly beneficial to a user because these enable the user to preview what skin could look like if the skin health either improves or deteriorates. This glimpse of the possible future condition of skin can strengthen the realization by the user and the subject (which may be the same person) of the importance of focusing upon skin health.

As shown in FIG. 1, to obtain a photo or video a camera 10 can be directed towards skin 12, which may be skin of a subject. The camera may be operated by a user to capture one or more images or video of the skin. The camera may be any type of camera, including a camera incorporated into a device, for example, such as a camera incorporated in a mobile device that is a smartphone 14.

It is preferable that the camera captures one or more images or video in a digital format, however in some embodiments of the present invention it may be possible to utilize a camera that does not create an image in digital format. In such an embodiment of the present invention, a conversion means can be utilized to convert the one or more images or video captured by the camera into a digital format. The conversion means may be integrated in the system of the present invention. An evaluation means operable to identify whether an image or video is in digital format or not, and to engage the conversion means if the image or video is not in digital format, may be integrated in the system of the present invention.

Figure 12:
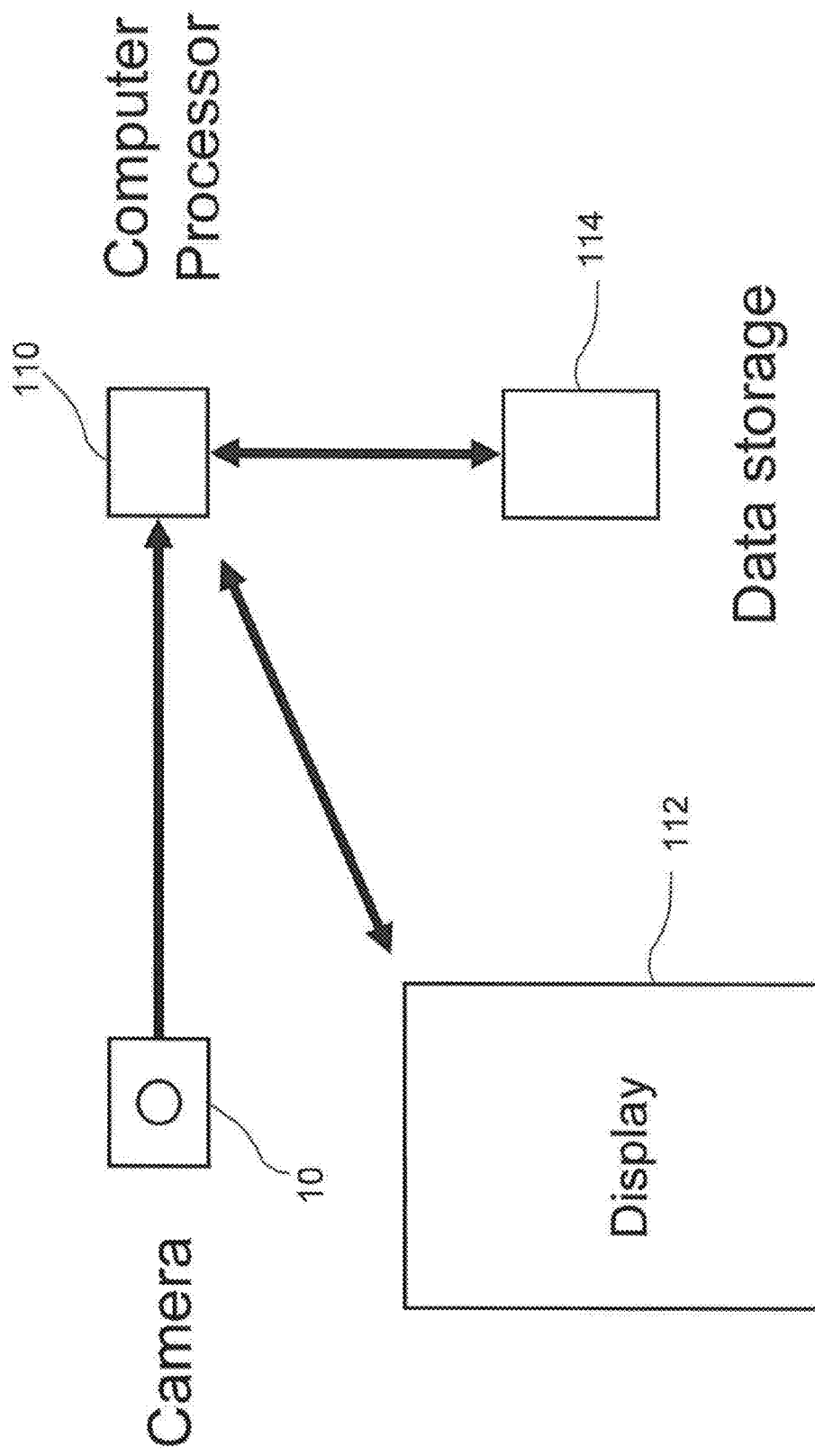
FIG. 12 shows a system diagram of a system of an embodiment of the present invention.

As shown in FIG. 12, a system of the present invention may incorporate multiple elements, including a camera 10 operable to capture one or more images or video showing the skin of a subject and to transmit said one or more images or video to a computer processor 110 via a wired or wireless connection. The computer processor is operable to execute the commands of a software application, as is described herein. The computer processor is further connected to data storage 114 by a wireless or wired connection. The data storage is operable to store data, and to receive and transmit data and to and from the computer processor. The computer processor is further connected to a display 112 operable to display information to a user, including information received by the display from the computer processor, for example, such as skin health information, overall skin health, or scores relating thereto.

The display may be a touch screen display whereby a user may utilize the display to: respond to questions posed to the user by the present invention, as described herein, and the responses of the user may be transmitted from the user's interaction with the display to the computer processor; to navigate through screens or other display elements displayed to a user on the display in an interactive manner; to provide instructions or commands to the system; and/or to otherwise engage interactively with the screens or invention generally.

Alternatively, a keyboard, mouse, and/or other communication means, may be connected either wirelessly or via a wired connection to the system, including to the computer processor element of the system, whereby a user may respond to queries posed to said user, navigate screens, provide instructions or commands, and/or otherwise engage interactively with the invention.

Embodiments of the present invention as described herein, may be wirelessly connectable to the Internet or an intranet to access information and download the software application and any updates, amendments or modifications thereto.

Figure 2:
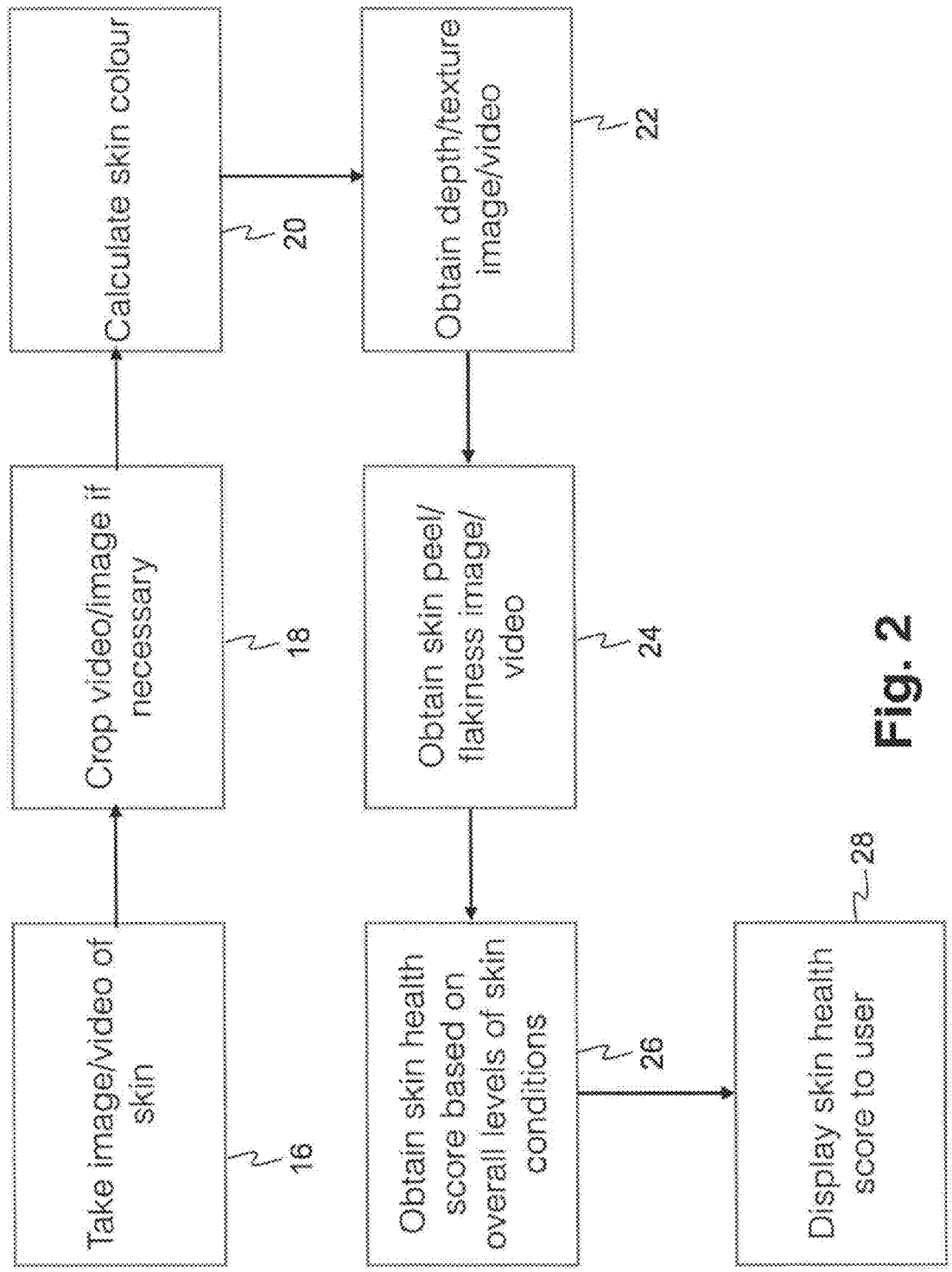
FIG. 2 is a flow chart of steps for processing the image and/or video, in accordance with an embodiment of the present invention.

As shown in FIG. 2 the process of the present invention starts with the image or video showing the subject's skin being captured 16 by the camera.

The digital image or video is transmitted from the camera, or any conversion means, to the system of the present invention by a transmission means operable to transmit the image or video to the computing device of the system that is operating the software application, or to data storage accessible by the computing device.

Video to be processed by the software application may be identified as a collection of multiple frames.

As further shown in FIG. 2, each frame or image may be cropped 18 before it is analyzed. Cropping may be performed to exclude superfluous or extraneous outer portions of the original frame or image, such as any border, any shaded or blurry edges, or any other outer portion of the frame or image. An image or video frame may be cropped in the case that such cropping is deemed necessary.

A cropped frame or image results in the generation of a new cropped image that differs in content than the original frame or image in that it does not include the outer portions that have been cropped away from the original frame or image.

For ease of reference and clarity of the description of the present invention herein, the image to be utilized in Steps 1-4 below will be referenced as image V. Image V may be the original received image or video frame, or it may be the cropped image resulting from the cropping process if cropping was deemed necessary. The analysis and processing module will utilize image V and perform a series of steps, including steps 1-4 below.

Step 1—

Image V will be blurred. The blurred image may be utilized to measure the skin colour 20. This step may involve either: (i) a determination of average skin colour; or (ii) a determination of average skin patch. The measurement of skin colour involves processes directed to the red, green and blue components of skin colour. Each of these components in the skin colour will be measured by applying either or both of the following approaches: (a) averaging either across multiple images or multiple video frames; or (b) averaging across the spatial "x" and "y" dimensions of each image or video frame. For ease of reference and clarity of the description of the present invention herein, the skin colour will be referenced as C.

The measurement of average skin patch is based on the deviations from the average patch that could be detected. If average skin patch is utilized by the invention it may be referenced as C, but when utilizing average skin patch C is not a single constant, it is a function of the "x" and "y" indexes.

The determinations of average skin patch or average skin colour may each be utilized as a baseline from which deviations of skin shown in the image or video from an average can be analyzed and otherwise investigated.

Step 2—

A calculation will be undertaken to determine the depth/texture 22 of image V. For ease of reference and clarity of the description of the present invention herein, the depth/texture will be referenced as T. As an example, a calculation such as the following may be utilized: $T(x,y)=C-V(x,y)$ if $C>V(x,y)$, else $T(x,y)=0$. The calculation is repeated for each of the red, green, and blue channels of the video frame or image. The sum of all of the pixels of T is utilized to determine the measure of the overall depth/texture of image V.

Step 3—

The peel or flake of the skin 24 shown in image V will be calculated. For ease of reference and clarity of the description of the present invention herein, flake will be referenced as F. As an example, a calculation such as the following may be utilized: $F(x,y)=V(x,y)-C$ if $V(x,y)>C$, else $F=0$. The sum of all of the pixels of T is utilized to determine a measure of the overall flakiness of image V.

Step 4—

The redness of image V will be calculated. For ease of reference and clarity of the description of the present invention herein, redness will be referenced as R. As an example, a calculation such as the following may be utilized: R with $Rr(x,y)=(Vr(x,y)/(Vg(x,y)+Vb(x,y)+Vr(x,y)))-(Cr/(Cg+Cr+Cb))$. In such a calculation Vr is denoted as the red channel of image V, and so on. R only has a single red channel, with all other colour channels being zero. The sum of the pixels of R is utilized to determine the measure of the overall redness of image V.

The above process of steps 1-4 can be repeated for all frames in a video, or for multiple images if multiple images are provided to the system. These steps generally relate to the analysis of an image or video to identify one or more skin conditions in the skin shown in the image or video. A skilled reader will recognize that other steps may be added to the analysis of the present invention that may identify other skin conditions not specifically referenced herein.

The results of the process of steps 1-4 repeated for all frames in a video can produce information about the skin health of the skin shown in the image or video, including skin health results. A skin health score, such as may be based on the skin health results, and scores relating to skin conditions may be displayed to a user on the display unit, or otherwise provided to a user.

The analysis by the system of the image or video will produce a skin health score 26. Some embodiments of the present invention determine skin health by way of a summation of the overall depth/texture, peel/flake, and redness of the image or video. If multiple images or video frames are utilized the summations for each image or video frame may be added. The results of the addition may be normalized and a weighted average may be achieved to produce the overall skin health score.

In the cases of the summations undertaken by embodiments of the present invention, a sum can be calculated over all video frames or across all of the multiple images. A summation of an image or video frame may be calculated over all pixels in the image or video frame, for example over "x" and "y" indexes for image $1(x,y)$). A summation over multiple images and video frames may also be generated.

The overall skin health score and components of the overall skin health score may be displayed to a user on the display unit, or otherwise provided to a user.

Rotating Capture of Images

Figure 11:
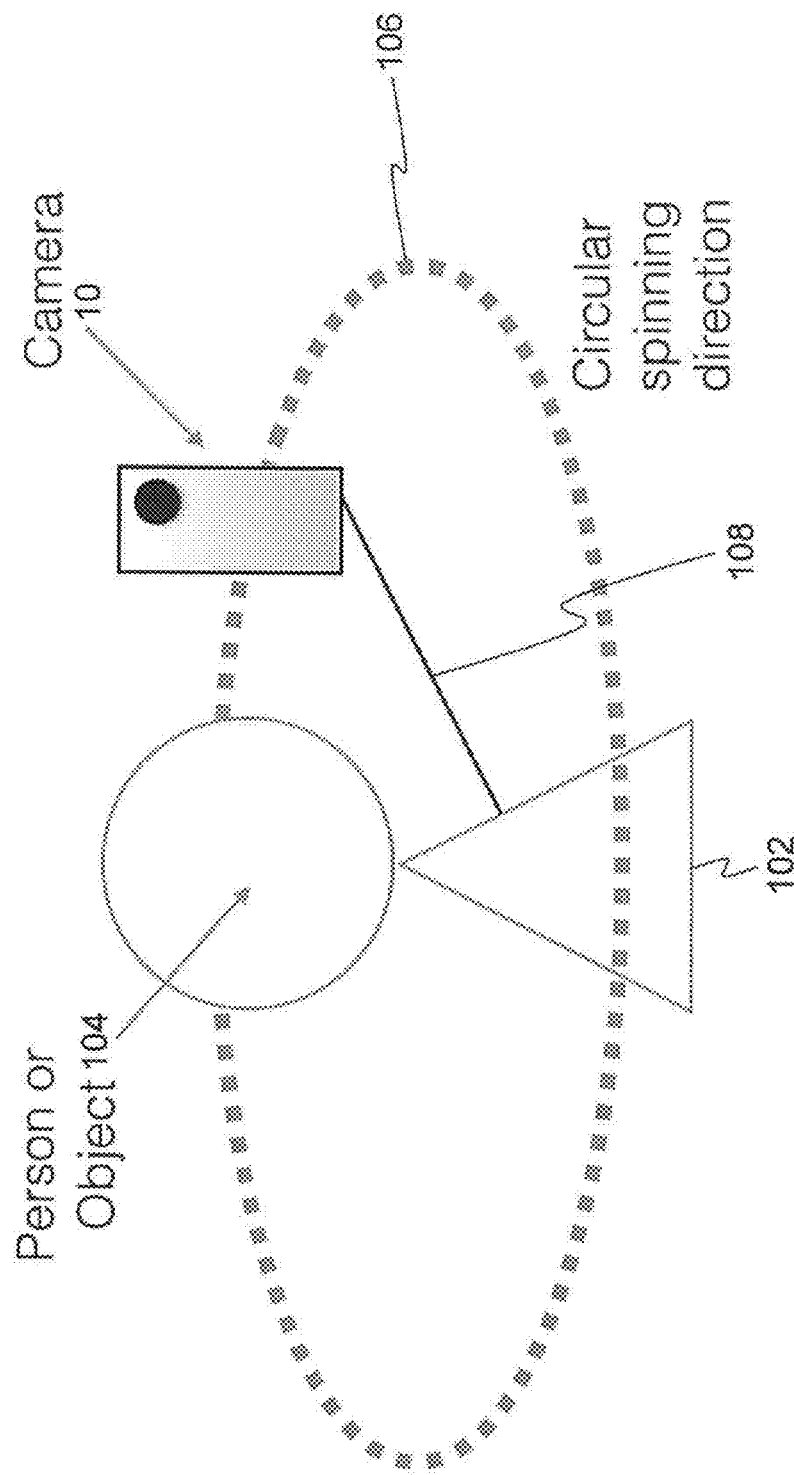
FIG. 11 shows a camera connected to an apparatus that permits the camera to be rotated around an axis while it captures one or more images of skin located within the area that the camera rotates around, in accordance with an embodiment of the present invention.

The present invention may also include a rotation apparatus upon which the camera may be mounted, as shown in FIG. 11. The rotation apparatus 102 is operable to move the camera 10 so that it rotates around an axis. While the camera is mounted and is in rotation, the camera may be capturing either video or multiple images of a subject's skin 104 located within the area 106 around which the camera is rotating. Through the use of the rotation apparatus the camera may capture video or images of a single subject's skin, but from various viewpoints (e.g., front, back and multiple sides).

The rotation apparatus may incorporate an arm 108 upon which the camera may be mounted. The arm may rotate from a base that either positions the arm above or below the subject, and mounts the camera to extend from and above, or from and below the arm. For example, if the subject is standing the base may affixed to a ceiling or pole so that the arm is positioned above the subject and the camera is mounted to extend downwards from the arm. In this configuration the arm will not contact the subject as the camera rotates around the subject. The arm will also not appear in any of the images or video captured by the camera.

Alternatively, the base may be positioned below a riser upon which a subject is standing or sitting, and the arm will extend from the base below the subject with the camera mounted to extend above the arm. In this configuration the arm will not contact the subject as the camera rotates around the subject or appear in any of the images or video captured by the camera.

As another alternative, the rotational apparatus may be configured to rotate along a vertical plane or a plane between vertical and horizontal. For example, such as to be operable to rotate around a subject's outstretched arm that is in a raised position.

This differs from other embodiments of the invention that generally involve capturing one or more images or video of the skin of a subject from a single viewpoint. The rotation apparatus may further be preferable to taking images or video while walking around a subject while the camera is handheld as the angle and distance between the subject and the camera may be known to the software application if the rotation apparatus is utilized and the position of the subject within the rotation of the rotation apparatus is provided to the software application. This can be helpful in determining effects of moving a camera about a subject upon the captured images or video, such as shadows, lighting, background, distance from a subject, angles and other effects that may show up in the images or video.

In some embodiments of the present invention, the rate of rotation of the person or mechanism holding the camera, as well as the circumference and exact track of the rotation (e.g., whether circular, oblong or otherwise) may be controlled by the present invention, as may be any unison or virtual unison rotation of the mechanism holding the camera and the subject.

The rotational apparatus and camera mounted thereon may be integrated in the system of the present invention. The images or video captured by the camera mounted upon the rotation apparatus can be provided to the software application for processing in accordance with the method and system of the present invention.

This apparatus may be utilized to capture targeted skin areas, such as skin in the facial area, or any other body part location, from a variety positions as the camera rotates around the subject's face or other skin area. In this manner multiple images will be captured having varying conditions reflected therein, such as varying lighting conditions, and other conditions, as well as varying positions. In some instances the images may also be captured from varying angles. Embodiments of the present invention may be operable to undertake corrections to address such variations.

For example, one embodiment of the present invention may apply the following to correct for lighting variations in images captured through the use of a rotation apparatus.

Step A—

A video or multiple images that form a set of images having a common object of interest, namely the skin of an area of a subject's body, may be captured by a camera, and the camera and subject may be stationary relative to each other as both objects rotate in unison, or virtually in unison, with respect to other conditions in an environment, such as light sources.

Step B—

The captured video or set of images may be aligned so that the object of interest in the various images or video frames are aligned. The lighting may be adjusted in the frames by the application of one or more of the following: colour averaging; filtering; histogram equalization; histogram stretching or histogram replacement; or patch replacement. The result may be the generation of a new colour corrected set of images or video.

Step C—

A single colour corrected image or the full colour corrected video may be displayed to a user. The colour corrected image or video may be utilized for analysis and processing by the system of the present invention.

Step D—

After the tracking of the object of interest is completed, colour correction can be achieved by any one or more of the following:

Colour Averaging—

The average colour values across the multiple images or video frames for tracked pixels may be utilized as the colour corrected pixel value. As an example, if a particular pixel on the face of subject, as shown in one or more images or video frames is tracked across multiple images or video frames, the average of the red, green, and blue channels may be utilized as the true pixel colour representation.

Colour Filtering—

This approach is similar to Colour Averaging, but rather than applying averaging a more complex filter is applied, such as a median filter, a filter to identify x % brightest pixel (wherein x ranges between 0 and 100), a filter to identify x % most saturated pixel (wherein x ranges between 0 and 100), or other filters applicable to tracked pixels.

Histogram Equalization—

Colour distribution may be equalized across tracked skin patches shown in the images or video frames by maximizing the dynamic range of the pixels based on available patches taken from the same location of the subject's skin shown across multiple images or video frames.

Histogram Stretching/Replacement—

The histogram relating to an image showing specific patches of skin may be adjusted by either stretching the histogram or replacing the histogram with a histogram from the patch image of the same location of the subject's skin shown in a different image or video frame.

Patch Replacement—

A part of an image or video frame may be replaced with a section of another image or video frame showing the same portion of the subject's skin.

In an embodiment of the present invention, a person may hold a camera and utilize the camera to capture images or video of a subject within the area that the person holding camera rotates around. In this embodiment there is no camera arm, but there is a mechanism to rotate the person around the rotational circumference.

In embodiments of the present invention, the rotational circumference that the camera rotates around, while held by a person or a holder, may be 360 degrees or a lesser distance. The subject may remain stationary in relation to the camera, or may rotate in unison, or virtually in unison, with the rotation of the camera.

In embodiments of the present invention, the rotational apparatus and related method can be used to extract the background shown in images or video captured by the camera in the rotational apparatus. The extracted background may be replaced by: (i) detecting the pixel motions as the camera and/or object are rotating; (ii) using the pixel motions to differentiate fixed items, for example, such as the subject or the person holding the camera, and moving items (i.e., the background); and (iii) substituting the moving pixels with an alternate background.

Simulation of Improving or Deteriorating Skin

Displays of simulations of either improved conditions of the skin shown in the image or video, or deteriorated conditions of the skin shown in the image or video may be generated by the present invention. Simulation produces a visualization of a skin condition in an improved or deteriorated state that can be displayed to a user.

A simulation of an improved condition is achieved by subtracting each specific image or video frame (multiplied by a scaling factor) for the original or cropped image or video frame (i.e., for image V). A simulation of a deteriorated condition is achieved by adding each specific image or video frame (multiplied by a scaling factor) to the original or cropped image or video frame (i.e. image V). The simulation produces a new image that may be displayed to the user as a visualization of an improved or deteriorated skin condition.

The scaling factor may be set through a variety of means, and it is possible for embodiments of the present invention to incorporate one or more of the following means to set the scaling factor: (i) automatically, such as by hard coding, in the software application; (ii) by the user through the use of a scaling factor adjusting means, such as may be provided to a user through a user interface element within the software application; and/or (iii) automatically by the application based on the subject's skin history and/or the subject's skin goals (the latter option being available in embodiments of the present invention that incorporate the option of the subject's skin goals being transmitted to the system and utilizable by the system for purposes such as setting the scaling factor).

For example, if the original video image or frame (i.e., image V) is O, then a redness increased version of would be O(x,y)=O(x,y)+a R(x,y) with "a" being a scaling factor and this addition being performed for each of the red, green, and blue channels.

If the scaling factor is large, the simulation acts as an amplification of a specific skin feature (for example, such as redness, flakiness, or any other skin feature that is identifiable by the present invention). Thus, a large scaling factor simulates a deterioration of skin that can be displayed to a user.

If the scaling factor is small or negative, it acts as an attenuation of a skin feature. Thus, a small or negative scaling factor simulates an improvement of skin that can be displayed to a user.

Combining Frames of a Video

The present invention may utilize a single image, multiple images, or a video showing the skin of a subject. If multiple images or video are provided for processing and analysis, a method can be applied that combines the multiple images or video frames and thereby enhances the results of analysis by combining the results of the analysis of the individual images or individual video frames.

For example, in one embodiment of the present invention, the simplest method of combining the results of individual images or video frames may consist of: (i) performing the skin quantification process described in Steps 1-4 above on each image or each video frame; and (ii) averaging skin health scores across all images or frames in the video.

Figure 6:
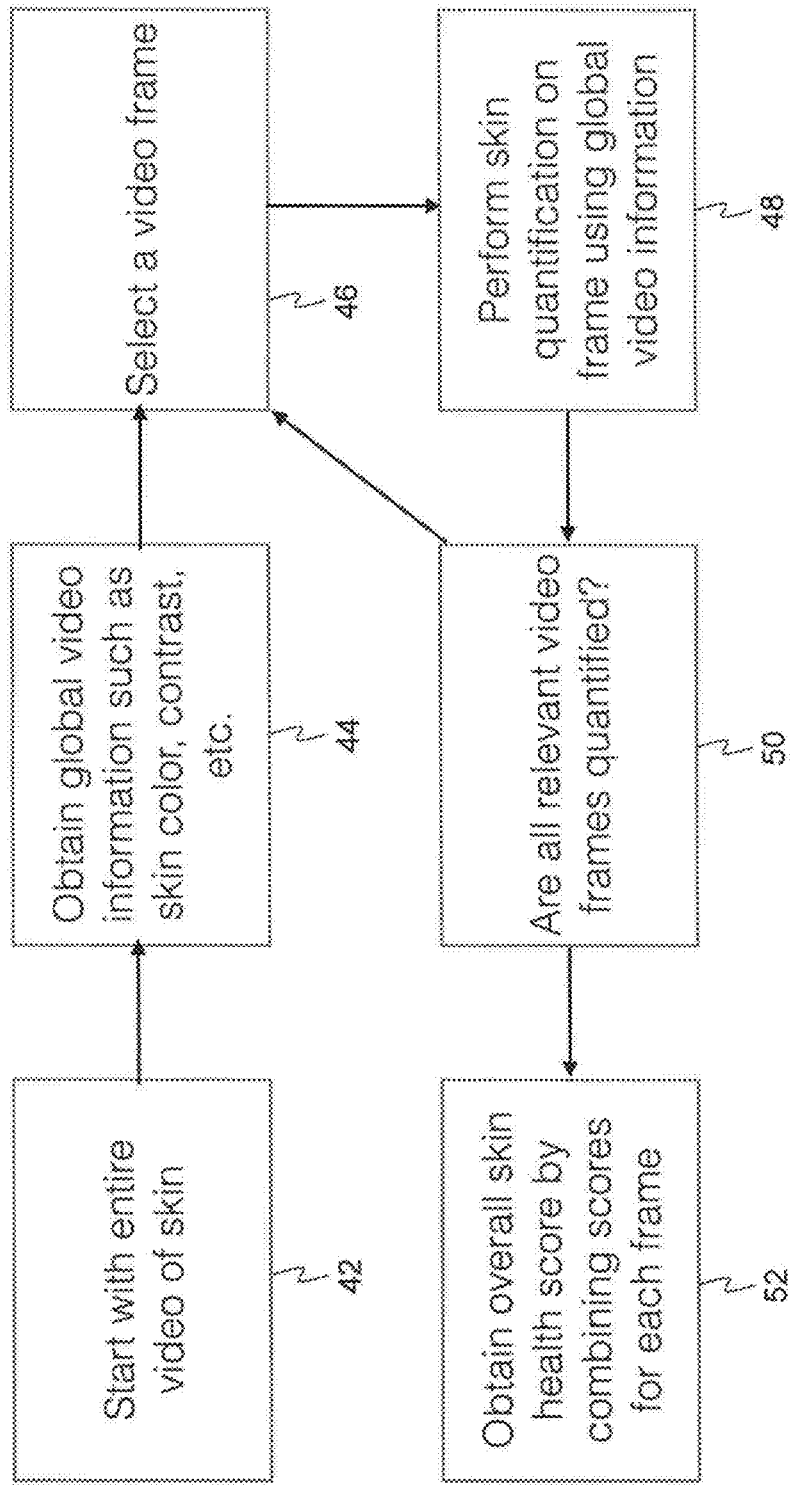
FIG. 6 is a flow chart of steps for evaluating health of skin from a video and/or image in accordance with an embodiment of the present invention.

In another embodiment of the present invention, another method for combining the results across multiple images or video frames may be applied to produces more effective results. As shown in FIG. 6, video or multiple images of the subject's skin must be obtained 42 by the system. Global information relating to the video or multiple images 44 is obtained from all images or frames in the video. This global information could consist of lighting, skin colour, focus, contrast, brightness, saturation, gamma, or any other information that could be extracted globally from the video frame.

Global information can be extracted from the original captured image or video during processing of said image or video. Determining each aspect of global information, such as lighting, skin colour, focus, contrast, brightness, saturation, gamma, etc., may involve the computation of a particular statistic over the image or video. As an example, the global information relating to a lighting aspect specifically may indicate the overall brightness of the image or video. As another example, the global information relating to an average skin colour aspect specifically may indicate the average red, green and blue channel over all the pixels in the image or video. A skilled reader will recognize that other global information aspects may be determined by way of similar approaches.

A particular image or video frame is selected 46. A skin quantification is performed 48 on each frame or image using global information. This skin quantification consists of determining skin health results and/or scores based on the depth/texture, peeling/flakes, and redness of the image or video in a method similar to that disclosed as Steps 1-4 herein.

An evaluation occurs after the skin quantification is performed on each frame or image to determine if there are subsequent images or frames to be selected 50. If frames or images exist for which a skin quantification has not been performed then the next of such frames or images is selected and a skin quantification is performed on that frame or image. The evaluation of the existence of any remaining frames or images for which a skin quantification has not been performed and selection of such frames or images and a skin quantification on such frames or images continues until there are no longer any frames or images for which a skin quantification has not been performed.

An overall skin health score is obtained 52 by combining the skin quantification scores of each frame or image. Skin quantification scores are determined based on the skin heath scores relating to depth/texture, peeling/flakes and redness in an image or video, in a method similar to that described in Steps 1-4 herein.

Next the system will generate an overall skin health score that is a function of the individual skin scores for each frame. Said function could consist, without limitation, of averaging, median filtering, taking the minimum (i.e. the worst case score), taking the maximum (i.e. the best case score), and weighting averaging (i.e., based on certain weights obtained from each frame).

An example of a means of generating an overall skin health score that is applied in some embodiments of the present invention involves multiple images or a video having multiple video frames. This example means of generating an overall skin health score involves combining results and/or scores determined for multiple images or video frames. Such a combination may allow the system to generate results that are more relevant and accurate than are otherwise achievable by extracting erroneous images or video frames that are determined as possible to result in out-of-focus, misdirected, or otherwise affected by issues that detract from the accuracy of the determination of overall skin health of a subject. The images or frames that are extracted are not utilized by the system in the determination of overall skin health of a subject. This improves the overall effectiveness and accuracy of the determinations of overall skin health achieved by the present invention.

The determination of overall skin health in accordance with embodiment of the present invention may involve the following:

a. Each image or frame is divided into a specified set of sections, for example, such as four quadrants, and a skin health score for each section of each image or video frame is determined.

b. Determine the maximum, minimum, median or other statistical measures for each section of each image or frame.

c. Utilize the measures for each section of each image or frame to determine an overall image or frame score for each image or frame.

d. Determine the overall skin health score by applying a statistical operation to the image or frame score. For example, the statistical operation may include determining the average of the highest x % of frame scores (with x ranging from 0 to 100), determining the average of the lowest x % of image or frame scores, determining the median image or frame scores, or determining the mode.

Skin Condition Indicator Example

The present invention is operable to identify aspects of skin determinable from either an image or video, as well as user responses to certain queries in some instances, to highlight the existence of skin conditions or potential skin conditions of a subject, as well as a determination and possibly a visualization as to how these relate to skin health. Herein a number of possible aspects of skin that can be used to identify skin conditions are discussed. Each aspect is utilized because it can indicate particular implications for skin health. To exemplify how an aspect can indicate particular implications for skin health a discussion of the role of the skin aspect of redness is offered.

Notably, a skilled reader will recognize that a discussion of redness is offered merely to provide a detailed example of a possible skin aspect that is utilized by the present invention. Other skin aspects and parameters are utilized by the present invention and each may have particular implications for skin health. Redness is not addressed particularly in this section to suggest it has a role in isolation, or a role that is more important than other skin aspects and/or parameters, but merely to provide one example of the potential importance of skin aspects and parameters generally.

The redness of skin can provide an indication of several skin health issues, including a number of skin conditions, such as psoriasis or allergic reaction, as well as several other skin conditions or health issues. To analyze redness a skin health score may be determined in accordance with the following red ratio formula:

$$R(x,y)/R(x,y)+G(x,y)+B(x,y)$$

where $R(x,y)$, $G(x,y)$, and $B(x,y)$ are the red, green and blue image or video frame channels at pixel location $(x,y)$. The red ratio formula provides results indicating the percentage of the colour intensity in each pixel that is red. Variations of the ratio, compared to a blurred version of the image or frame, can be an indication of skin health issues or skin conditions by indicating above average redness of the skin shown in an image or video.

To determine a redness variation level the system may: (i) determine the amount of red in each pixel; (ii) determine the red variation by subtracting the amount of red in an image or video frame from a blurred version of the same image or video frame; and (iii) undertake addition of the results of the subtraction of (ii). The result achieved, once normalized, represents a level of variation for redness in relation to the image or video frame.

The level of variation for redness can be utilized to identify possible skin health issues or skin conditions that may be affecting the skin shown in the image or video frame.

Skin Component Filter

Steps 1-4 may involve various means of detecting specific features of the skin, for example, such as redness or flakiness. In embodiments of the present invention the detection of specific features of the skin can involve the application of various filters to the image or video. Filters can consist of a colour difference and gradient between the actual image pixel and the detected skin color. The application of the filter to the image or video acts to separate features of relevance from other artifacts on the skin.

The application of a filter may include applying a tuned filter to a skin image. The tuned filter may be configured to incorporate a combination of deviation from skin color, the gradient of the image, as well as the color of the pixel. The application of the tuned filter to the image or video will produce a result that captures a specific aspect of the skin, for example, such as redness or dryness. The result of the application of the tuned filter to the image or video frame may produce a new image that is a filtered image. The filtered image will specifically show an aspect of the skin, such as redness or any other aspect of the skin that can be determined through the application of a filter tuned to identify that aspect of the skin.

The application of a filter in embodiments of the present invention may involve an image or video filtering processing operation that, determines a statistical measure for a particular pixel in an image or video frame based on a comparison to other pixels in the image or video frame, and in particular to neighbouring pixels. The determined statistical measure results in a new value being generated in relation to the particular pixel. Filters may be linear or non-linear.

Linear filters may require the use of a convolution matrix that is convolved with the image or video frame to define a filtered image. For example, a filter that equates each pixel with the difference between the original pixel and a pixel from a blurred image may be utilized to create a high pass effect, whereby only sudden and abrupt deviation from the skin are left after filtering.

Further subjecting the output of a linear filter to solely positive values will result in a non-linear filter where what is left is only spots and/or deviations indicating where the original pixel is brighter than the blurred pixel. This example of a non-linear filter corresponds to a filter that may be focused on identifying areas of the skin that are any of white, peeled, or flaky. By focusing on negative results of a linear filter it is possible to achieve a non-linear filter that corresponds to a filter that is focused on identifying areas of the skin that are any of dark, dark spots, shadowed, or textured. As yet another example, a non-linear filter focusing on areas of the skin that are red spots or red areas can be achieved by focusing solely on the positive filter coefficients in the red channel, or by reviewing the percentage of red colour in each pixel.

Filters may be applied to each individual image and video frame. Filters may be stored in the system, for example, such as on a server, or in data storage, and in some embodiments of the present invention one or more filters may be stored in a mobile device. Filters stored on a server may particularly be capable of being modified and/or having machine learning algorithms, or other calculations, applied thereto to improve the filter efficiency and accuracy. Such improvement to a filter may occur in particular over a period of time.

Filter output can be utilized to amplify and attenuate particular aspects of the image or video frame. Filter output can also be summed to result in a score representing a particular aspect of the skin shown in the image or video frame.

Figure 3:
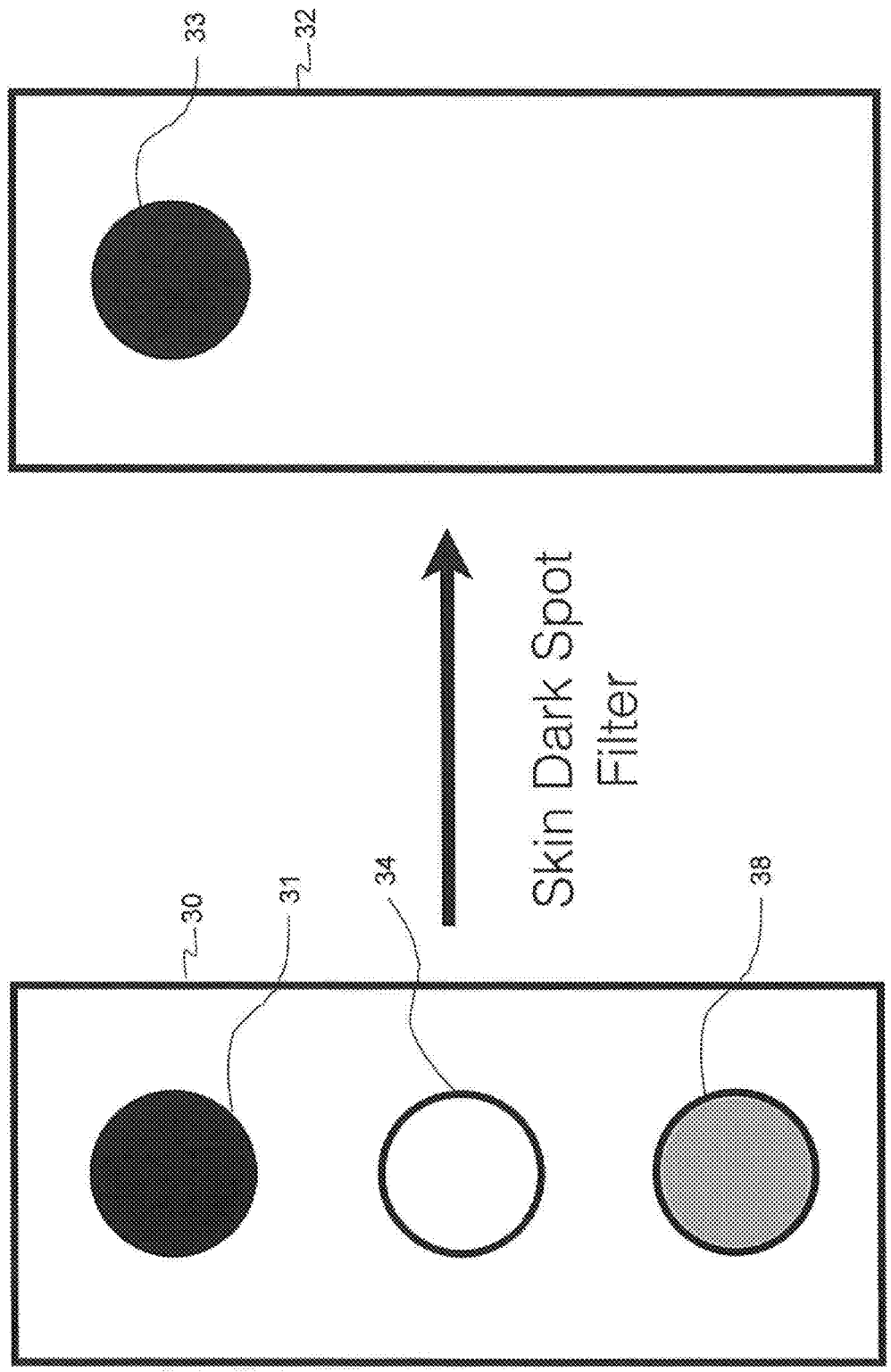
FIG. 3 shows a skin filter operable to detect dark spots on skin, in accordance with an embodiment of the present invention.

For example, as shown in FIG. 3 an image or video frame 30 may incorporate a variety of different colours (e.g. at the pixel level), for example, such as colours that include at least one dark colour 31, at least one white colour 34 and at least one red colour 38. Notably, the image or video frame 30 is shown in FIG. 3 to highlight only three examples of colours at a pixel level in the image or video, but this is for example purposes only. An image or video can include multiple pixels that are of a variety of colours within the dark, white and red colour ranges. A skin dark spot filter may be applied to the image or video frame to produce a dark spot filtered image 32 that highlights one or more dark colour spots 33, that may be one or more dark pixels in the image or video. Notably, the dark spot filtered image shown in FIG. 3 highlights only a single dark colour spot for example purposes, but there may be multiple dark colour spots highlighted in a dark spot filtered image generated by the present invention. The dark spot filtered image may show the aspect of dark spots in relation to the skin shown in the image or video frame that was filtered. In particular, the dark spot filtered image will show primarily the dark and/or brown patches of skin.

Figure 4:
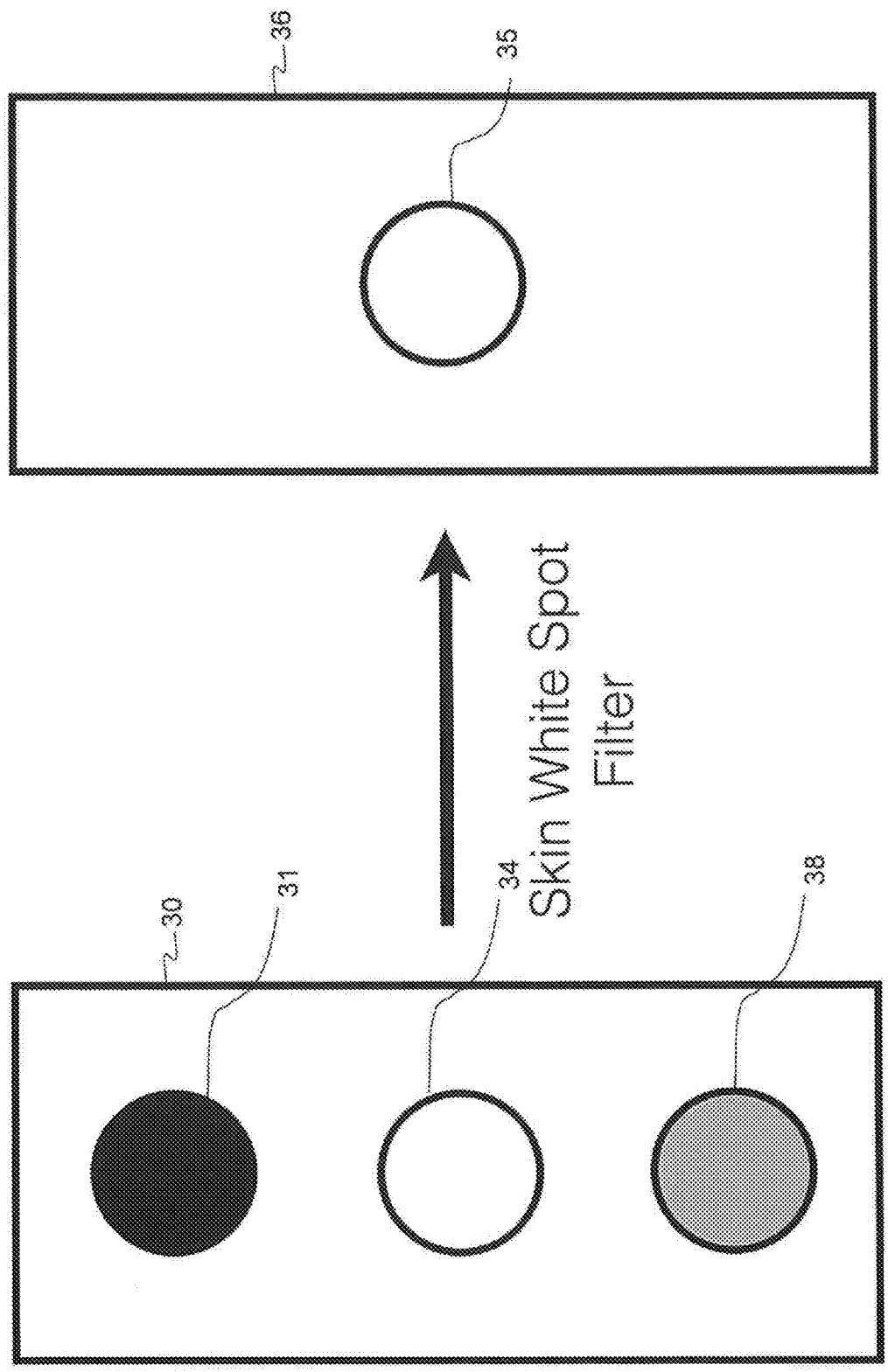
FIG. 4 shows a skin filter operable to detect white spots on skin, in accordance with an embodiment of the present invention.

As another example, as shown in FIG. 4 an image or video frame 30 may incorporate a variety of different colours (e.g., at the pixel level), for example, such as colours that include at least one dark colour 31, at least one white colour 34 and at least one red colour 38. Notably, the image or video frame 30 is shown in FIG. 4 to highlight only three examples of colours at a pixel level in the image or video, but this is for example purposes only. An image or video can include multiple pixels that are of a variety of colours within the dark, white and red colour ranges. A skin white spot filter may be applied to the image or video frame to produce a white spot filtered image 36 that highlights one or more white colour spots 35, that may be one or more white pixels in the image or video. Notably, the white spot filtered image shown in FIG. 4 highlights only a single white colour spot for example purposes, but there may be multiple white colour spots highlighted in a white spot filtered image generated by the present invention. The white spot filtered image may show the aspect of white spots in relation to the skin shown in the image or video frame that was filtered. In particular, the white spot filtered image will show primarily the white and/or flaky patches of skin.

As another example, as shown in FIG. 5 an image or video frame 30 may incorporate a variety of different colours (e.g., at the pixel level), for example, such as colours that include at least one dark colour 31, at least one white colour 34 and at least one red colour 38. Notably, the image or video frame 30 is shown in FIG. 5 to highlight only three examples of colours at a pixel level in the image or video, but this is for example purposes only. An image or video can include multiple pixels that are of a variety of colours within the dark, white and red colour ranges. A skin red spot filter may be applied to an image or video frame to produce a red spot filtered image 40 that highlights one or more red colour spots 39, that may be one or more red pixels in the image or video. Notably, the red spot filtered image shown in FIG. 5 highlights only a single red colour spot for example purposes, but there may be multiple red colour spots highlighted in a red spot filtered image generated by the present invention. The red spot filtered image may show the aspect of red spots in relation to the skin shown in the image or video frame that was filtered. In particular, the red spot filtered image will show primarily the red patches of skin.

Smartphone Application

One embodiment of the present invention may be a mobile device application, for example, such as a smartphone application. Generally, when a smartphone is referenced herein the reference is to be understood to include any mobile device.

In this embodiment of the present invention, a camera incorporated in the smartphone may be utilized to capture an image or video of a subject's skin and to process and analyze such image or video in accordance with the software application described herein.

Figure 14:
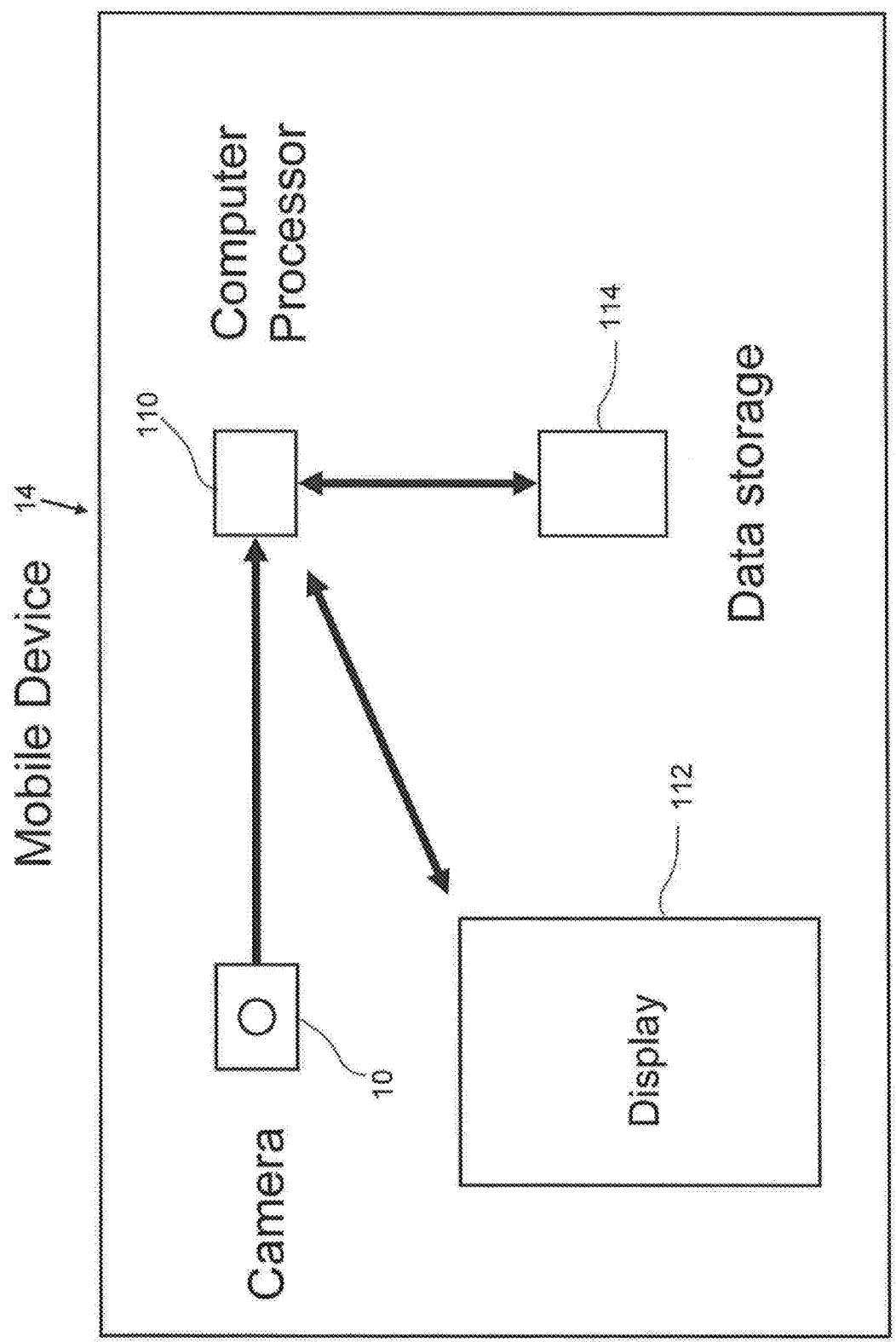
FIG. 14 shows a system diagram of a mobile device system embodiment of the present invention.

As shown in FIGS. 14 and 15 the system of the present invention may be wholly enclosed in a mobile device, such as a smartphone or other mobile device. In such an embodiment of the present invention, a camera 10 may be integrated in the mobile device 14 and connected therein to a computer processor 110 positioned within the mobile device. The computer processor may execute commands of a software application stored within the mobile device and in accordance with commands of the software application instruct a user to operate the camera to capture one or more images or video of a subject's skin in a manner whereby said one or more images or video may be processed and analyzed as described herein. The computer processor is further operable to receive and transmit data to and from data storage 114 located within the mobile device and wherein data, including results, scores and other information generated by the present invention is stored.

The computer processor is further connected to a display 112 of the mobile device, and the display is operable to display information to a user, including information received by the display from the computer processor, for example, such as skin health information, overall skin health, or scores relating thereto. The display may be a touch screen display whereby a user may utilize the display to respond to questions posed to the user by the present invention and navigate screens, as described herein. The responses and commands of the user may be transmitted from the user's interaction with the display to the computer processor. Alternatively, the mobile device may incorporate a keyboard utilizable by the user to transmit query responses and commands to the computer processor.

Figure 13:
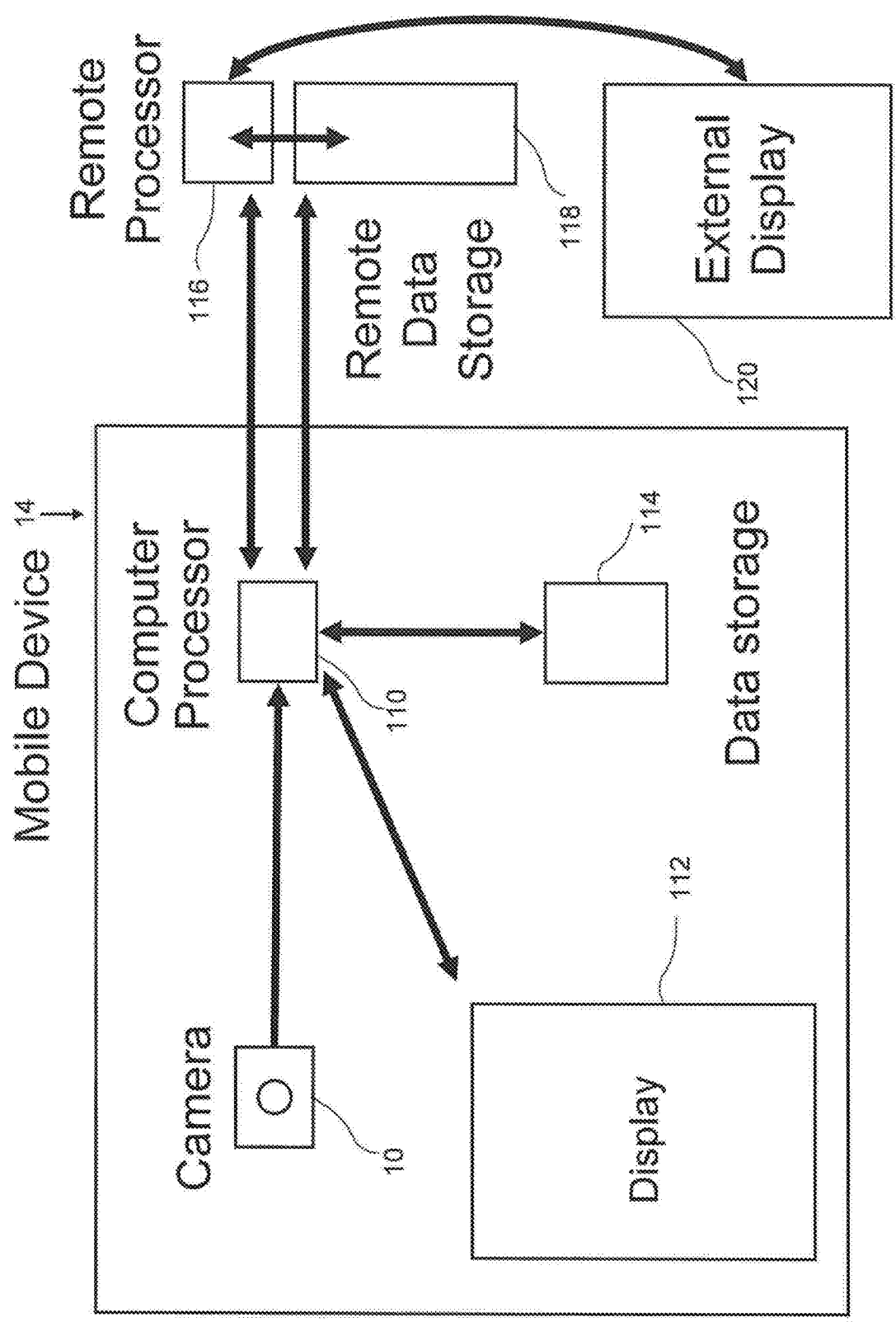
FIG. 13 shows a system diagram of a mobile device system incorporating remotely located elements as well as a mobile device, in accordance with an embodiment of the present invention.

As shown in FIG. 13 one embodiment of the present invention may incorporate a mobile device having a camera, computer processor, display and data storage integrated therein, and that is further connected, via a wired or wireless connection, to additional external system elements, for example, such as a remote processor 116, remote data storage 118, and/or an external display 120. The additional system elements external to the mobile device may be utilized to enhance the function of the present invention. For example, the remote data storage may be operable to store data or information that is generated by the present invention, or that is accessed by the present invention from external sources, as described herein. As another example, the remote processor may execute commands of the software application of the present invention that relate to data stored in the remote data storage, for example, such as previous images or video as described herein, or that relate to elements external to the mobile device, for example, such as accessing information obtained from sources remote to the mobile device, us described herein. Also, in some embodiments of the present invention the remote processor may execute any commands of the software application and thereby improve the efficiency and processing speed of the present invention.

As yet another example, the external display may be utilized to display information to a person or user located remotely from the mobile device, or in a form that is easier to view than via the display of the mobile device. This may be of particular assistance if a dermatologist or other skin health professional is viewing any of the viewable output of the present invention. The skin health professional may require the ability to view the displayed information remotely and/or may require a larger display, or otherwise different display capability, than is available on the mobile device.

An embodiment of the present invention incorporating a mobile device may be wirelessly connectable to the Internet or an intranet to access information and download the software application and any updates, amendments or modifications thereto, as required, and as described herein.

In another embodiment of the present invention, as shown in FIG. 16, the mobile device is wirelessly connectable to a remote server 124 and incorporates a transmission means 122 operable to wirelessly transmit information and other data to and from the remote server. The remote server may incorporate data storage, and be operable to store data generated by the present invention and transmit such stored data back to the mobile device. The remote server may further be operable to transmit information accessible by the remote server to the mobile device. The connection between the remote server and the mobile device may be direct, or may be via the Internet, an intranet, or some other wireless means.

Figure 7:
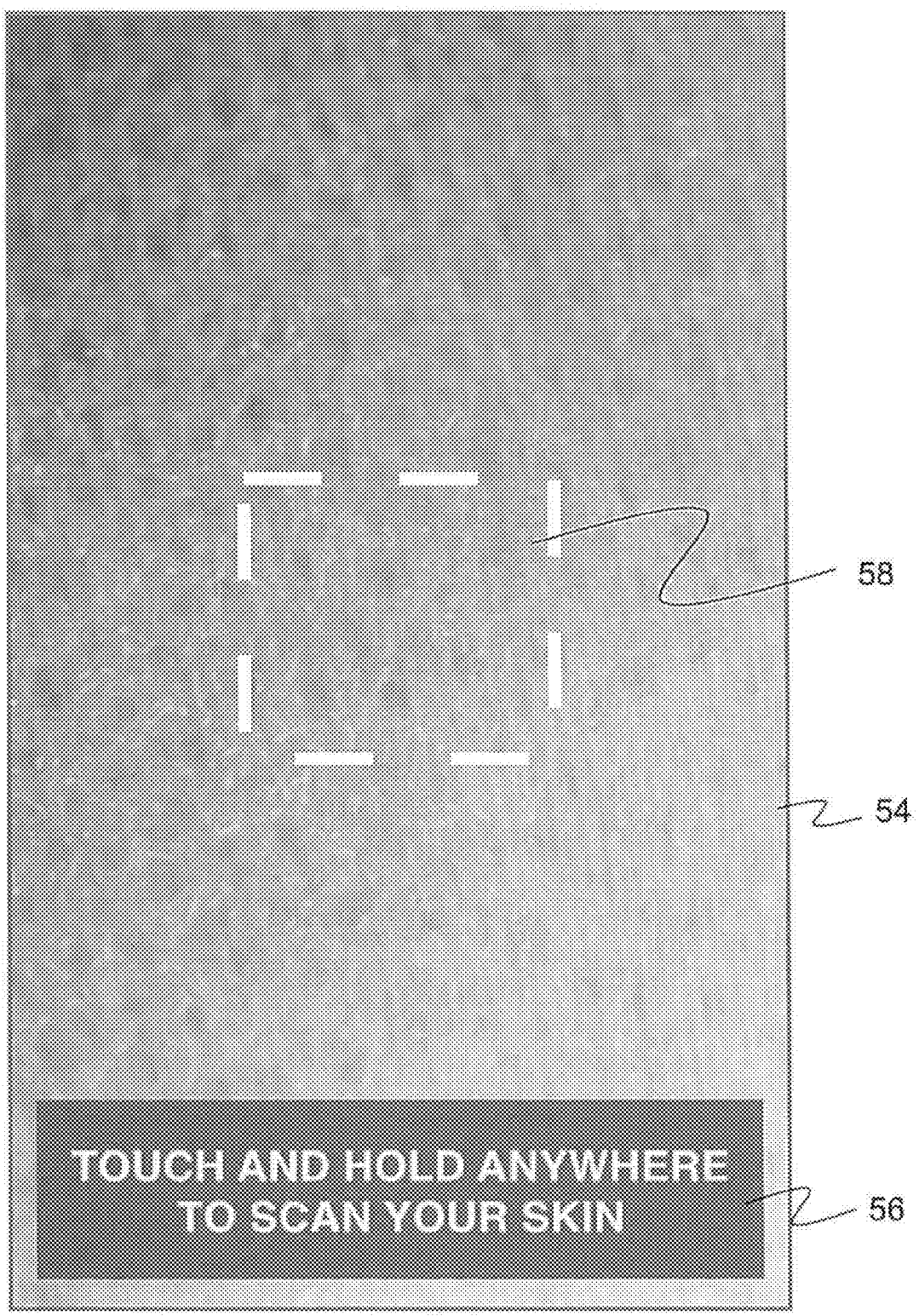
FIG. 7 is a smartphone application whereby a user can capture an image and/or video of skin, in accordance with an embodiment of the present invention.

The present invention incorporating a mobile device may include several screens to be displayed to a user or shown on the display unit of the mobile device. For example, a screen may be operable for the user to capture the image or video. An example of such a screen is that may be displayed on the smartphone and utilized by the user is shown in FIG. 7. The screen may show a skin view 54 as viewed through the lens of the camera. A focus section 58 may be shown on the screen that is utilizable to zoom in or out of an area of skin. An image/video capture button 56 may be provided and this button may provide instructions to the user for capturing an image or video of skin.

Once the captured image or video of skin is processed by the software application component of the smartphone or mobile application, the display unit of the smartphone may display information that provides information relating to the results of the skin analysis and processing of the system and/or provides options for information or activities relating to the skin analysis and processing.

(Embodiments of the present invention that do not incorporate a mobile device, or that incorporate an external display unit, may produce screens that are similar to the mobile device screens disclosed herein and shown in FIGS. 7-10, or that are different therefrom, in accordance with the information to be provided to a user, provided user navigation of screens, and user interactivity with screens, including user commands and instructions provided to the system, and other aspects of such embodiments of the present invention.)

Figure 8:
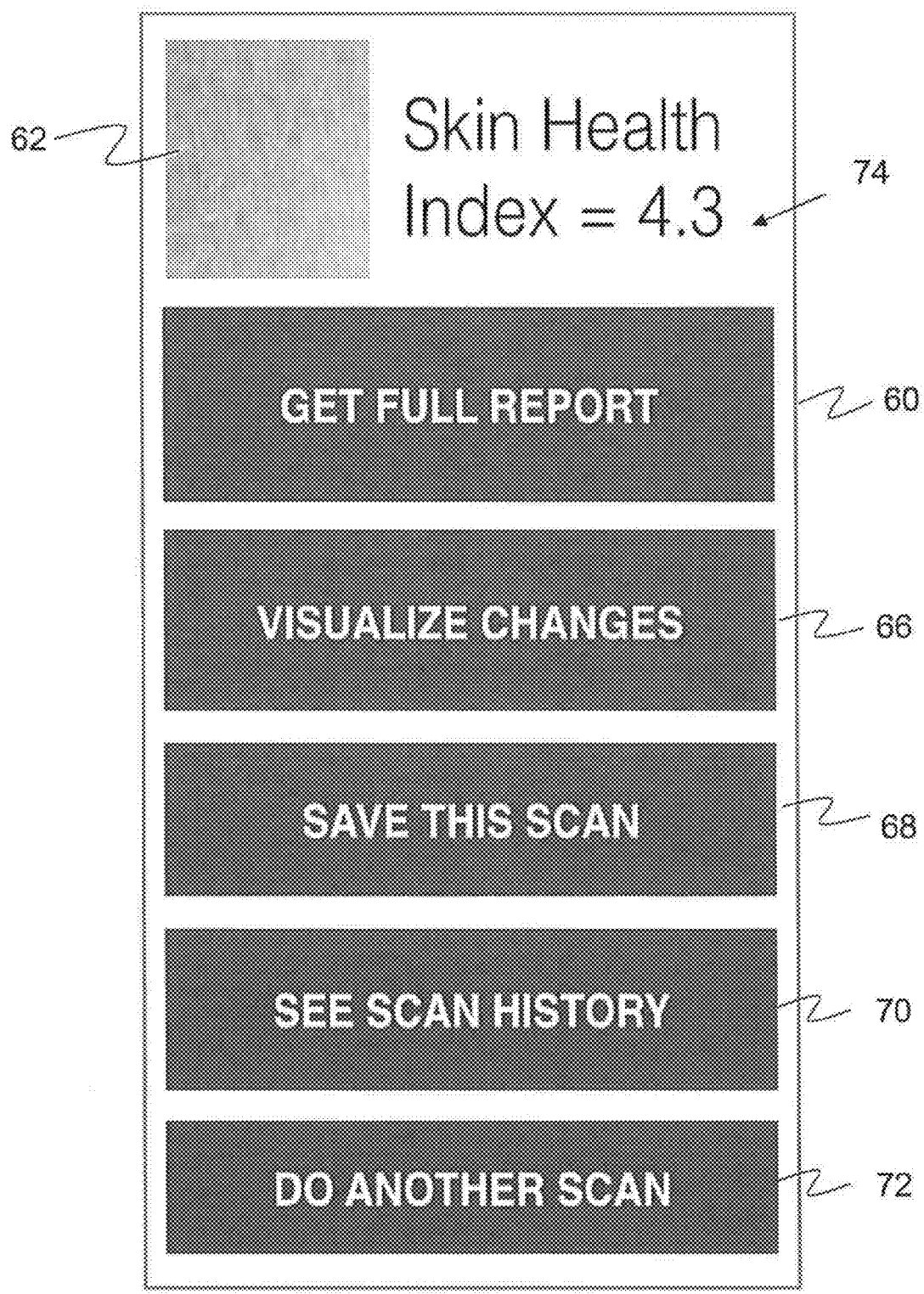
FIG. 8 is a smartphone application whereby a subject's skin health score is displayed, in accordance with an embodiment of the present invention.

An example of a mobile device information/option screen 60 is shown in FIG. 8. This screen displays the skin health index 74, including a view of an image or video 62. Options for analysis results and actions are provided as buttons. Each button may be chosen by the user, by way of a touch screen, mouse click, or other communication means operable to select the button, as provided by the mobile device.

In FIG. 8, two result related buttons are offered, namely a Get Full Report button 64 and a Visualize Changes button 66. Selecting the Get Full Report button will cause results of the processing and analysis of the system, as described herein to be displayed to the user. An example of such a display is shown in FIG. 9

Figure 9:
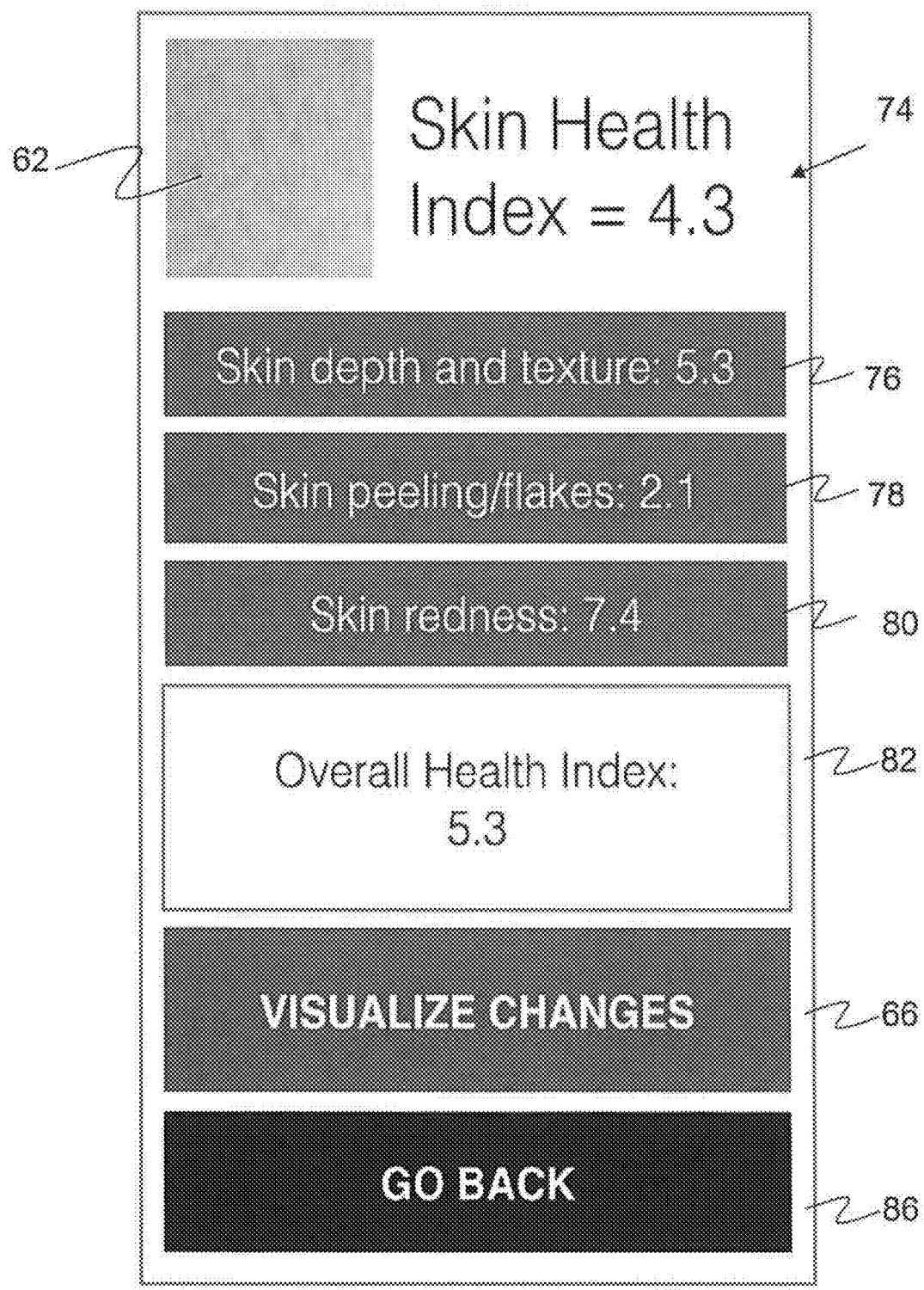
FIG. 9 is a smartphone application whereby a detailed skin health report including analysis relating to various skin conditions and issues is displayed, in accordance with an embodiment of the present invention.

FIG. 9. shows a display that provides the user with a skin health index, being the score relating to overall skin health as is determined by the present invention, as well as specific information relating one or more skin conditions and/or parameters, such as skin depth or texture score display 76, a skin peeling and/or flakes score display 78, and a skin redness score display 80. The score provided for each skin condition may indicate to the user the severity of each skin condition in relation to the skin shown in the image or video.

Specific skin health category results and/or scores may be calculated by taking into account solely a particular filter. Specific category scores are further generally normalized to be within a pre-defined range, for example, such as a range from 0 (indicating the lowest level of skin health) to 10 (indicating the highest level of skin health).

The overall health index score display 82 can be integrated into a display provided to a user 28, such as is shown in FIG. 9. It may also be possible for a user to select a score of a particular category shown and to drill down by using options available to the user to obtain more information and details relating to the specific category, or about the nature of the specific category. For example, a user may choose to select the score for redness and to drill down to have more information relating to the redness of the skin provided to the user, or to drill down to obtain more information about what redness may indicate relating to health issues or conditions.

A skilled reader will recognize that the present invention, in a mobile device software application configuration or another configuration of the present invention, may be organized so that a user may obtain various types of information and scores that are either generated by the system, or that are available to the system (e.g., in a connected server, hard disk memory of a device, the Internet, or any other source of information accessible by the system). Information and scores may be made available to a user by way of various screen layouts, drill down options, or other means incorporated in embodiments of the present invention.

A Go Back button 86, as shown in FIG. 9, can be provided in a screen to assist a user with navigating through the screens available in the smartphone application.

Selecting the Visualize Changes button, as shown in FIG. 9, will cause visualizations of simulations of improvements and/or deteriorations of the skin shown in the image or video to be displayed. An example of such a display is shown in FIG. 10.

Figure 10:
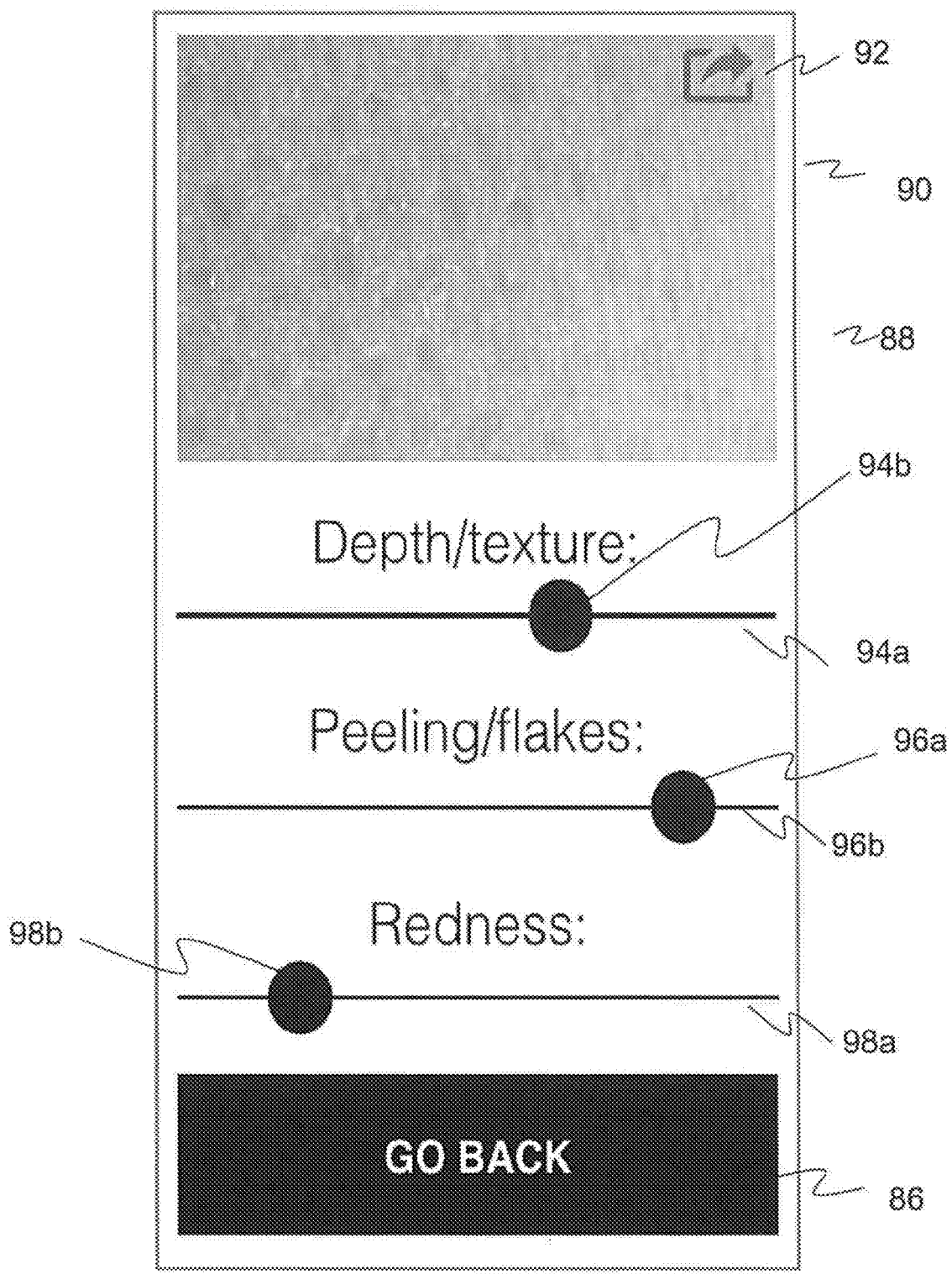
FIG. 10 is a smartphone application whereby the a visualization of the effects of skin health changes are displayed to a user, in accordance with an embodiment of the present invention.

As shown in FIG. 10, a simulation screen 88 can provide a simulation that offers a display of changes to the skin shown in the image or video, in accordance with a visualization of amplifying or attenuating different features relating to the skin. For example, the screen may incorporate a skin simulation section 90 that displays a visualization of a variety of skin simulation results. The skin simulation section may incorporate one or more activity option buttons 92 to enhance the simulation display. The simulation shown in the skin simulation section may be modified in accordance with choosing options for displaying a simulation that shows the results of variations of improvements or deteriorations of skin conditions. The simulation may incorporate a variety of types of skin conditions in a range of improvement or deterioration stages.

The choice of simulation improvement or deterioration level shown may be adjusted by the user. For this purpose the user may activate one or more slideable tabs each positioned along a range, and each tab and range may relate to a specific skin condition. The location where the tab is positioned along the range will either cause the simulation to show a visualization of the skin condition as improved or deteriorated. As examples, FIG. 10 shows a depth/texture tab 94*b* slideable along a depth/texture range, a peeling/flakes tab 96*a* slideable along a peeling/flake range 96*b*, and a redness tab 98*a* slideable along a redness range 98*b*. The tabs may be initially displayed to a user at a pre-determined location, for example, such as in the middle of an area of the screen, such as a sliceable area of the screen, or the tabs may be set a locations in the screen to correspond to category scores or information displayed to a user.

FIG. 8 also shows example action buttons that may be offered to the user, including a Save this Scan button 68, a See Scan History button 70 and a Do Another Scan button 72.

Selecting the Do Another Scan button will result in a screen that a user can utilize to capture an image or video of skin to appear, such as is shown in FIG. 7.

Selecting the Save this Scan button may cause the image or video most recently captured by the user, being the image or video 62 shown in the screen, to be stored. The image or video may be stored in available data storage, such as data storage in the smartphone, or may be transferred to remote data storage or a remote server. Transfer to remote data storage or a remote server may be by way of a wired or wireless means, and may be direct or through an intranet, the Internet or any other transmission means. The information stored may include solely the image or video, or may include the image or video as well as the processing and analysis results relating thereto, such as skin health results and overall skin health, or some subset of such processing and analysis results.

Selecting the See Scan History button may display information relating to prior images and videos captured by the user utilizing the smartphone application. The information about prior images and videos captured by the user may be provided as a list, as tiles, or in any manner compatible with the display unit of the smartphone. It may be possible that the user can select a previous captured image or video through use of the screen accessed through use of the See Scan History button. Additionally, it may be possible to access information relating to any selected image or video, including results of processing or analyzing of the video or image by the system of the present invention, such as skin health results and overall skin health. The image or video, and in some embodiments of the invention information relating thereto, such as skin health results and overall skin health, may be accessed from any storage location where such image or video and information is stored, as described herein.

The See Scan History may further incorporate an option whereby one or more images or videos that have been previously processed, analyzed or at least transmitted to the present invention can be utilized to conduct an assessment of improvement or deterioration of skin of the same subject over time. Previous images or videos may be stored by the system, for example, such as in data storage, a server, or a database, that is available on a mobile device or remotely. Information generated or received by the present invention generally in relation to said previous images or videos may also be stored with the images or videos, including any responses by a user to queries. For example, each database record relating to an image or video may indicate the date of capture of the image or video, the skin health scores and overall skin health scores relating to the image or video, user responses to queries relating to skin health, detailed health score reports, skin health results and scores, overall skin health and scores, new images or video generated based on the processing (such as filtered images or video), or any other information or scores relating to the image or video, the processing and analysis of the image or video, or obtained from other sources (such as the Internet or remote servers) relating to the image or video. Sets of images or videos relating to a particular subject and to a specific area of a subject's skin may be so indicated in the database, as may be the date of the processing and analyzing of the previous images and videos, and/or the date of capture of the previous images or videos.

An embodiment of the present invention, may offer a feature whereby information relating to the previous images or videos of a subject may be further processed or analyzed to produce results that indicate changes in skin over time for a subject generally, for a specific area of a subject's skin, or by other parameters. The user may choose the parameters for the processing and analysis, such as the period of time when the previous images or videos were captured, whether all areas of skin of as subject or only specific locations of skin of a subject should be processed and analyzed. A skilled reader will recognize that other parameters for such an activity of processing and analyzing previous images and videos are possible.

A comparison of previous images and videos to each other and/or to any image or video of the same subject being processed and/or analyzed at the present time may also be achieved by the present invention.

This feature of the present invention may allow for a review of changes in the skin health (including related skin health results and scores, and overall skin health and scores) of a subject over time, or even showing the images or video so that changes in skin health overtime may be seen by a user either side-by-side or in close proximity. Changes in skin health may thereby be evaluated, by a user, a dermatologist, a skin health professional, or any other person having been provided with access to the images or video, including the previous images and video and the results of the processing and analysis thereof by the system. The changes in skin health indicated by the type of review that this feature of the present invention permits may indicate either improvement or deterioration of skin health over time. For example, a skin health score (or an overall skin health score) that increases overtime will indicate an improving skin heath and possibly the improvement of a skin issue or condition. Whereas a skin health score that decreases over time will indicate deteriorating skin health and possibly the deterioration or development of a skin issue, concern or condition.

The screens shown in FIGS. 7-10 are merely provided as examples of possible screen configurations and layouts to be integrated in the present invention. Other screen configurations and layouts, as well as other displayed information or activity options, may be integrated in screens in embodiments of the present invention.

Printable versions of processing and analysis results, as will as of images and video frames, may be generated by embodiments of the invention to be provided to a user.

Results of the processing and analysis of the present invention and the images or video may also be provided in a format by the present invention whereby it is transferrable to other persons and systems. For example, to a health worker (such as a remote health worker who may utilize the transferred information to assist with a diagnosis), or to a law enforcement officer or children's aid worker who may utilize the results to detect a skin condition indicating harm to the subject who's skin is shown in the image or video. There are a variety of instances and reasons why it would be advantageous for the present invention to make the results, scores and/or images or video available in a format that is easily shareable with others.

It will be appreciated by those skilled in the art that other variations of the embodiments described herein may also be practiced without departing from the scope of the invention. Other modifications are therefore possible.

I claim:

1. A skin health system operable to process and analyze a plurality of images or a plurality of frames of a video each captured by a camera or scan and each showing a subject's skin in accordance with a software application, said skin health system comprising:
   a. a computer processor operable to receive and process the plurality of images or plurality of frames in accordance with commands of the software application that include the following steps:
      i. extracting one or more global information parameters from an analysis of each of the plurality of images or each of the plurality of frames;
      ii. processing each of the plurality of images or each of the plurality of frames using the one or more global information parameters to generate respective skin health parameters; and iii. combining the respective skin health parameters to produce an overall skin health measure;
b. a data storage to store the plurality of images or the plurality of frames, the global information parameters, the respective skin health parameters, and the overall skin health measure; and
c. a display operable to display any of the plurality of images or the plurality of frames to a user, and to further display any of the global information parameters, the skin health parameters and the overall skin health measure;

wherein step (ii) comprises:
  A. blurring each image or each video frame to produce a blurred image or a blurred video frame and utilizing the blurred image or the blurred video frame to determine an average skin colour parameter or average skin patch parameter, said average skin colour parameter and average skin patch parameter being skin parameters;
  B. determining a dept or texture parameter of skin shown in each image or each video frame through an analysis of colour channels in each image or each video frame, said depth or texture parameter being one of the skin parameters;
  C. determining a peeling or flakiness parameter of the skin shown in-each image or each video frame, said peeling parameter being one of the skin parameters; and
  D. determining a redness parameter of the skin shown in each image or the video frame, said redness parameter being one of the skin parameters.

2. The skin health system of claim 1, wherein a camera is integrated in the skin health system, said camera being operable to capture the plurality of images or the plurality of frames.

3. The skin health system of claim 2, wherein the skin health system is provided in a mobile device.

4. The skin health system of claim 3, wherein the mobile device is a smartphone, tablet, or laptop, computer.

5. The skin health system of claim 3, wherein the mobile device is connected to one or more of the following: a remote processor a remote data storage; and an external display.

6. The skin health system of claim 2, wherein the camera is integrated in a rotational apparatus operable to rotate the camera around a subject so the camera can capture the plurality of images or the plurality of frames while rotating around the subject.

7. A skin health analysis method operable to determine overall skin health of skin of a subject shown in a plurality of images or a plurality of frames of a each captured by a camera or a scan, comprising the steps of:
a. a computer processor receiving and processing the plurality of images or the plurality of frames, said processing including the following steps:
  i. extracting one or more global information parameters from an analysis of each of the plurality of images or each of the plurality of frames;
  ii. processing each of the plurality of images or each of the plurality of frames using the one or more global information parameters to generate respective skin health parameters from one or more skin parameters, said processing involving the following steps:
    A. blurring each image or each video frame to produce a blurred image or a blurred video frame and utilizing the blurred image or the blurred video frame to determine an average skin colour parameter or average skin patch parameter, said average skin colour parameter and average skin patch parameter being skin parameters;
    B. determining a depth or texture parameter of skin shown in each image or each video frame through an analysis of colour channels in each image or each video frame, said depth or texture parameter being one of the skin parameters;
    C. determining a peeling or flakiness parameter of the skin shown in each image or each video frame, said peeling or flakiness parameter being one of the skin parameters; and
    D. determining a redness parameter of the skin shown in each image or the video frame, said redness parameter being one of the skin parameters; and
b. the computer processor combining the respective skin health parameters to produce an overall skin health measure;
c. displaying any of the plurality of images or the plurality of frames to a user, and to further display any of the global information parameters, the skin parameters, the skin health parameters, and the overall skin health measure; and
d. storing one or more of the following in a data storage: at least one of the plurality of images or the plurality of frames; the global information parameters; the skin parameters; the skin health parameters; and the overall skin health measure.

8. The skin health analysis method of claim 7, further comprising the step of generating one or more visualizations depicting amplification or attenuation of the skin health parameters.

9. The skin health analysis method of claim 7, further comprising the step of applying one or more filters to each of the plurality of images or each of the plurality of frames to produce filtered images that highlight and identify specific characteristics of each of the plurality of images or each of the plurality of frames.

10. The skin health analysis method of claim 7, further comprising the step of applying one or more of the following filters to each of the plurality of images or each of the plurality of frames to produce filtered images: a dark spot filter to identify dark spots; a white spot filter to identify white spots; and a red spot filter to identify red spots.

11. The skin health analysis method of claim 10, further comprising determining skin conditions or skin issues relating to the skin shown in each of the plurality of images or each of the plurality of frames, after applying the respective dark spot filter, white spot filter and red spot filter, including peeling skin, flaky skin, dry skin, red skin, shadowed skin, or darkened skin.

12. The skin health analysis method of claim 7, further comprising the further steps of: utilizing the components of a mobile device to facilitate the steps of the method; and utilizing the camera of the mobile device to capture the plurality of images or the plurality of frames.

13. The skin health analysis method of claim 7, further comprising the steps of: applying weighted averages to each of the skin health parameters to produce weighted average results; and utilizing the weighted average results to determine the overall skin health measure.

14. The skin health analysis method of claim 7, further comprising the steps of generating skin health scores based on the skin health parameters and the overall skin health measure; and reporting the skin health scores to the user by displaying the skin health scores to the user on the display unit.

15. The skin health analysis method of claim 7, further comprising the step of generating one or more screens incorporating the skin health parameters and the skin health measure, said one or more screens being operable for the user to navigate through the one or more screens to access the skin health parameters and the overall skin health measure when said one or more screens are displayed to the user.

16. The skin health analysis method of claim 7, further comprising the steps of generating skin health questions and displaying said skin health questions to a user; receiving a response to each of the skin health questions provided by the user utilizing each response in combination with the skin health parameters to determine the overall skin health measure.

17. The skin health analysis method of claim 7, further comprising the steps of: accessing previous skin health analysis information relating to the subject from the data storage; displaying the previous skin health analysis information to a user on the display unit with the skin health parameters and the skin health result; and analyzing the previous skin health analysis information and the skin health parameters and the overall skin health measure to determine any improvement or deterioration of any skin condition or skin issue of the subject.

18. The skin health analysis method of claim 7, further comprising the steps of: displaying the plurality of images or the plurality of frames and the skin health parameters and the overall skin health measure to a user, said user being a skin health professional to assist the skin health professional to diagnose one or more skin conditions of the subject.

* * * * *